US012752110B2

(12) United States Patent
Ching et al.

(10) Patent No.: US 12,752,110 B2
(45) Date of Patent: Oct. 6, 2026

(54) SYSTEM AND METHOD FOR NON-INVASIVE BRAIN STIMULATION OF COGNITIVE ENHANCEMENT

(71) Applicant: Washington University, St. Louis, MO (US)

(72) Inventors: ShiNung Ching, St. Louis, MO (US); Todd Braver, St. Louis, MO (US); Matthew Singh, St. Louis, MO (US); Jacob Wheelock, St. Louis, MO (US)

(73) Assignee: Washington University, St. Louis, MO (US)

( * ) Notice: Subject to any disclaimer, the term of this patent is extended or adjusted under 35 U.S.C. 154(b) by 361 days.

(21) Appl. No.: 18/334,249

(22) Filed: Jun. 13, 2023

(65) Prior Publication Data

US 2023/0398353 A1 Dec. 14, 2023

Related U.S. Application Data

(60) Provisional application No. 63/351,707, filed on Jun. 13, 2022.

(51) Int. Cl.
*A61N 1/36* (2006.01)

(52) U.S. Cl.
CPC ................................ *A61N 1/36031* (2017.08)

(58) Field of Classification Search
CPC .............. A61N 1/36031; A61N 1/0456; A61N 1/36025
See application file for complete search history.

(56) References Cited

U.S. PATENT DOCUMENTS

| | | | | |
|---|---|---|---|---|
| 2012/0209346 | A1* | 8/2012 | Bikson | A61N 1/36034 607/45 |
| 2019/0126033 | A1* | 5/2019 | Pradeep | A61B 5/4812 |
| 2019/0134395 | A1* | 5/2019 | Fitzgerald | A61N 1/36025 |

OTHER PUBLICATIONS

"Estimation and validation of individualized dynamic brain models with resting state fMRI", NeuroImage vol. 221, Nov. 1, 2020, 117046) (Year: 2020).*

Singh et al. ("Scalable surrogate deconvolution for identification of partially-observable systems and brain modeling", Journal of Neural Engineering, vol. 17, No. 4, Published Aug. 4, 2020.*

Alexei Verkhratsky and Vladimir Parpura Calcium signalling and calcium channels: evolution and general principles European Journal of Pharmacology Sep. 15, 2014 1-3 739 Elsevier Amsterdam, Netherlands.

(Continued)

*Primary Examiner* — Amanda L Steinberg
*Assistant Examiner* — Philip C Edwards
(74) *Attorney, Agent, or Firm* — Armstrong Teasdale LLP

(57) ABSTRACT

A non-invasive closed-loop transcranial electrical stimulation (tES) system is described. The tES system includes a stimulator configured to generate transcranial electrical current to a head of a subject and a tES computing device. The tES computing device is programmed to receive neuroelectrical signals acquired from the head of the subject while being stimulated with the transcranial electrical current and exogenously modify brain activities of the subject by the transcranial electrical current based on endogenous neural control mechanisms of the subject via a control loop having the neuroelectrical signals as reference signals to the stimulator.

20 Claims, 30 Drawing Sheets

(56) References Cited

OTHER PUBLICATIONS

Earl K. Miller and Jonathan D. Cohen An Integrative Theory of Prefrontal Cortex Function Annual Review of Neuroscience 2001 167-202 24 Annual Reviews San Mateo, California.
Erwin Neher and Bert Sakmann The patch clamp technique Scientific American Mar. 1, 1992 44-51 266-3 Springer Nature Berlin, Germany.
Fabio Pasqualetti, Sandro Zampieri, Francesco Bullo Controllability metrics, limitations and algorithms for complex networks American Control Conference Apr. 6, 2014 3287-3292 Institute of Electrical and Electronics Engineers Inc. Portland, Oregon.
Hayley Thair, Amy L. Holloway, Roger Newport, and Alastair D. Smith Transcranial Direct Current Stimulation (tDCS): A Beginner's Guide for Design and Implementation Frontiers in Neuroscience Nov. 27, 2017 11 Frontiers Media Lausanne, Switzerland.
Hector J Sussmann Lie Brackets and Real Analyticity in Control Theory Mathematical Control Theory Banach Center Publications Jun. 7, 1905 14 Polish Scientific Publishers Warsaw, Poland.
Jacob Wheelock A Real-Time Transcranial Current Stimulation Platform Apr. 29, 2022 Washington University in St. Louis Electrical and Systems Engineering Undergraduate Research St. Louis, Missouri.
John R. Stroop Studies of interference in serial verbal reactions Journal of Experimental Psychology 1935 643-662 18-6 American Psychological Association Washington, D.C., U.S.
Jonathan D. Cohen, Todd S. Braver, and Randall O'reilly A computational approach to prefrontal cortex, cognitive control and schizophrenia: recent developments and current challenges Philosophical Transactions of the Royal Society B Oct. 29, 1996 1515-1527 351 Royal Society London, UK.
Jonathon D. Cohen, Gary Aston-Jones, and Mark S. Gilzenrat A Systems-Level Perspective on Attention and Cognitive Control: Guided Activation, Adaptive Gating, Conflict Monitoring, and Exploitation versus Exploration Cognitive neuroscience of attention Jul. 16, 2004 71-90 N/A The Guilford Press New York, New York.
Joset A. Etzel, Rachel E. Brough, Michael C. Freund, Alexander Kizhner, Yanli Lin, Matthew F. Singh, Rongxiang Tang, Allison Tay, Anxu Wang, Todd S. Braver The Dual Mechanisms of Cognitive Control dataset, a theoretically-guided within-subject task fMRI battery Scientific Data Mar. 29, 2022 9 Nature Portfolio Berlin, Germany.
Matthew F. Singh, Anxu Wang, Michael W. Cole, Shinung Ching, Todd S. Braver Enhancing Task fMRI Preprocessing via Individualized Model-Based Filtering of Intrinsic Activity Dynamics NeuroImage Feb. 15, 2022 247 Elsevier Amsterdam, Netherlands.
Matthew F. Singh, Anxu Wang, Todd S. Braver, Shinung Ching Scalable surrogate deconvolution for identification of partially-observable systems and brain modeling Journal of Neural Engineering Aug. 4, 2020 17 IOP Publishing Bristol, UK.
Matthew F. Singh, Michael W. Cole, Todd S. Braver, and Shinung Ching Developing control-theoretic objectives for large-scale brain dynamics and cognitive enhancement Annual Reviews in Control Jul. 5, 2022 363-376 54 Elsevier Amsterdam, Netherlands.
Matthew F. Singh, Michael Wang, Michael W. Cole, Shinung Ching Efficient identification for modeling high-dimensional brain dynamics American Control Conference Jun. 10, 2022 Institute of Electrical and Electronics Engineers Inc. Atlanta, Georgia.
Matthew F. Singh, Todd S. Braver, Michael W. Cole, Shinung Ching Estimation and validation of individualized dynamic brain models with resting state fMRI NeuroImage Nov. 1, 2020 221 Elsevier Amsterdam, Netherlands.
Michael Deflorian and Susanne Zaglauer Design of Experiments for nonlinear dynamic system identification IFAC Proceedings Volumes Jan. 11 13179-13184 44 Elsevier Amsterdam, Netherlands.
Oscar Miranda-Domínguez, Jon Gonia, Tay I. Netoff Firing rate control of a neuron using a linear proportional-integral controller Journal of Neural Engineering Oct. 26, 2010 7-6 IOP Publishing Bristol, UK.
Owen P. Hamill, Alain Marty, Erwin Neher, Bert Sakmann, and Fred J. Sigworth Improved patch-clamp techniques for high-resolution current recording from cells and cell-free membrane patches Pflügers Archiv Aug. 81 85-100 391 Springer Science+Business Media Berlin, Germany.
Roger W. Brockett Feedback Invariants for Nonlinear Systems IFAC Proceedings Volumes Jun. 1, 1978 1115-1120 11-1 Elsevier Amsterdam, Netherlands.
Shi Gu, Fabio Pasqualetti, Matthew Cieslak, Qawi K. Telesford, Alfred B. Yu, Ari E. Kahn, John D. Medaglia, Jean M. Vettel, Michael B. Miller, Scott T. Grafton, and Danielle S. Bassett Controllability of structual brain networks Nature Communications Oct. 1, 2015 6 Nature Portfolio Berlin, Germany.
Shinung Ching Control-Theoretic Approaches for Modeling, Analyzing, and Manipulating Neuronal (In)activity Dynamic Neuroscience Mar. 9, 2018 219-238 N/A Springer Berlin, Germany.
Shun-Min Samuel Wang, Yi-Jing Juang, Jia-Jin Jason Chen, Chun-Wei Wu, Chien-An Chen, Che-Wei Lin, Van-Truong Nguyen, and Chih-Wei Peng Designing and pilot testing a novel high-definition transcranial burst electrostimulation device for neurorehabilitation Journal of Neural Engineering Sep. 17, 2021 18-5 IOP Publishing Bristol, UK.
Todd Braver and Matthew Botvinick Motivation and cognitive control Annual Review of Psychology Jan. 15 83-113 66 Annual Reviews San Mateo, California.
Todd S. Braver The variable nature of cognitive control: a dual mechanisms framework Trends in Cognitive Sciences Feb. 12 106-113 16-02 Cell Press Cambridge, Massachusetts.
Vinod Menon and Lucina Q. Uddin Saliency, switching, attention and control: a network model of insula function Brain Structure and Function May 10 655-667 214 Springer Science+Business Media Berlin, Germany.
Vinod Menon Large-scale brain networks and psychopathology: a unifying triple network model Trends in Cognitive Sciences Sep. 12, 2011 483-506 15-10 Cell Press Cambridge, Massachusetts.

* cited by examiner

SYSTEM AND METHOD FOR NON-INVASIVE BRAIN STIMULATION OF COGNITIVE ENHANCEMENT

CROSS REFERENCE TO RELATED APPLICATIONS

This application claims the benefit of and priority to U.S. Provisional Patent Application No. 63/351,707, filed Jun. 13, 2022, entitled "SYSTEM AND METHOD FOR NON-INVASIVE BRAIN STIMULATION OF COGNITIVE ENHANCEMENT," which is hereby incorporated by reference in its entirety.

STATEMENT REGARDING FEDERALLY SPONSORED RESEARCH & DEVELOPMENT

This invention was made with government support under SMA1835209 awarded by the National Science Foundation. The government has certain rights in the invention.

BACKGROUND

The field of disclosure relates to the development of technologies for brain stimulation.

The development of technologies for brain stimulation provides a means for scientists and clinicians to directly actuate the brain and nervous system. Brain stimulation has shown intriguing potential in terms of modifying particular symptom clusters in patients and behavioral characteristics of subjects. The stage is thus set for optimization of these techniques and the pursuit of more nuanced stimulation objectives, including the modification of complex cognitive functions such as memory and attention. Control theory and engineering will play a key role in the development of these methods, guiding computational and algorithmic strategies for stimulation. In particular, realizing this goal will require new development of frameworks that allow for controlling not only brain activity, but also latent dynamics that underlie neural computation and information processing. A need exists to address the current challenges and identify potential research pathways associated with exogenous control of cognitive function.

This background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

In one aspect, non-invasive closed-loop transcranial electrical stimulation (tES) system is provided The tES system includes a stimulator configured to generate transcranial electrical current to a head of a subject and a tES computing device. The tES computing device includes at least one processor in communication with at least one memory device. The tES computing device is programmed to receive neuroelectrical signals acquired from the head of the subject while being stimulated with the transcranial electrical current and exogenously modify brain activities of the subject by the transcranial electrical current based on endogenous neural control mechanisms of the subject via a control loop having the neuroelectrical signals as reference signals to the stimulator.

DETAILED DESCRIPTION

The disclosure includes systems and methods for non-invasive closed-loop transcranial electrical stimulation of a subject. As used herein, a subject is a human, an animal, or a phantom, or part of a human, an animal, or a phantom, such as a head. Method aspects will be in part apparent and in part explicitly discussed in the following description.

Figure 1:
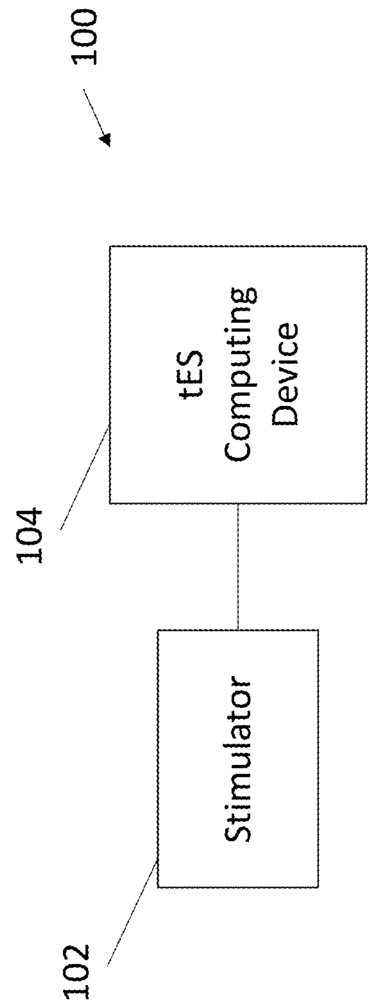
FIG. 1 is a block diagram of a non-invasive closed-loop transcranial electrical stimulation (tES) system.

FIG. 1 is a schematic diagram of an example non-invasive close-loop transcranial electrical stimulation system (tES) system 100. In the example embodiment, the systems 100 includes a stimulator 102 configured to generate transcranial electrical current to a head of a subject. The stimulator 102 includes a plurality of switches having a cathode and an anode and a microcontroller configured to control the plurality of switches and to provide an anodal stimulation or a cathodal stimulation.

In some embodiments, the stimulator 102 further includes variable resistance circuitry coupled with the microcontroller. The microcontroller is configured to adjust an amplitude of the transcranial electrical current by adjusting resistance in the variable resistance circuitry. In another embodiment, the stimulation 102 may further include a current regulator configured to limit a maximum amplitude of the transcranial electrical current.

In some embodiments, the stimulator 102 is configured to generate the transcranial electrical current in response to reference signals. In some embodiments, the stimulator is configured to run as an arbitrary waveform generator to generate an arbitrary waveform defined by an input.

Figure 2:
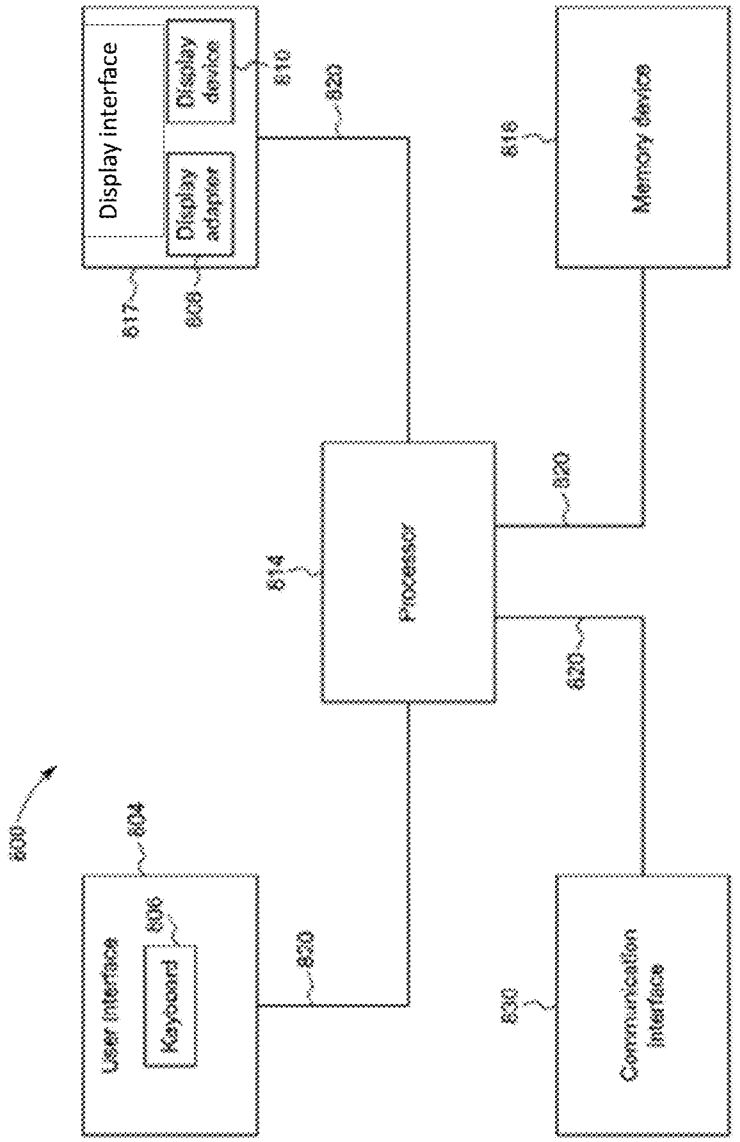
FIG. 2 is a block diagram of an exemplary computing device.

In the example embodiment, system 100 further include a tES computing device 104. The systems and methods described herein may be implemented in the tES computing device 104. The tES computing device 104 may be any suitable computing device and software implemented therein. FIG. 2 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a display interface 817 that presents information, such as input events and/or validation results, to the user. The display interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the display interface 817 may include an audio output device (e.g., an audio adapter and/or a speaker) and/or a printer.

The computing device 800 also includes a processor 814 and a memory device 818. The processor 814 is coupled to the user interface 804, the display interface 817, and the memory device 818 via a system bus 820. In the exemplary embodiment, the processor 814 communicates with the user, such as by prompting the user via the display interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not in-tended to limit in any way the definition and/or meaning of the term "processor."

In the exemplary embodiment, the memory device 818 includes one or more de-vices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

Figure 3:
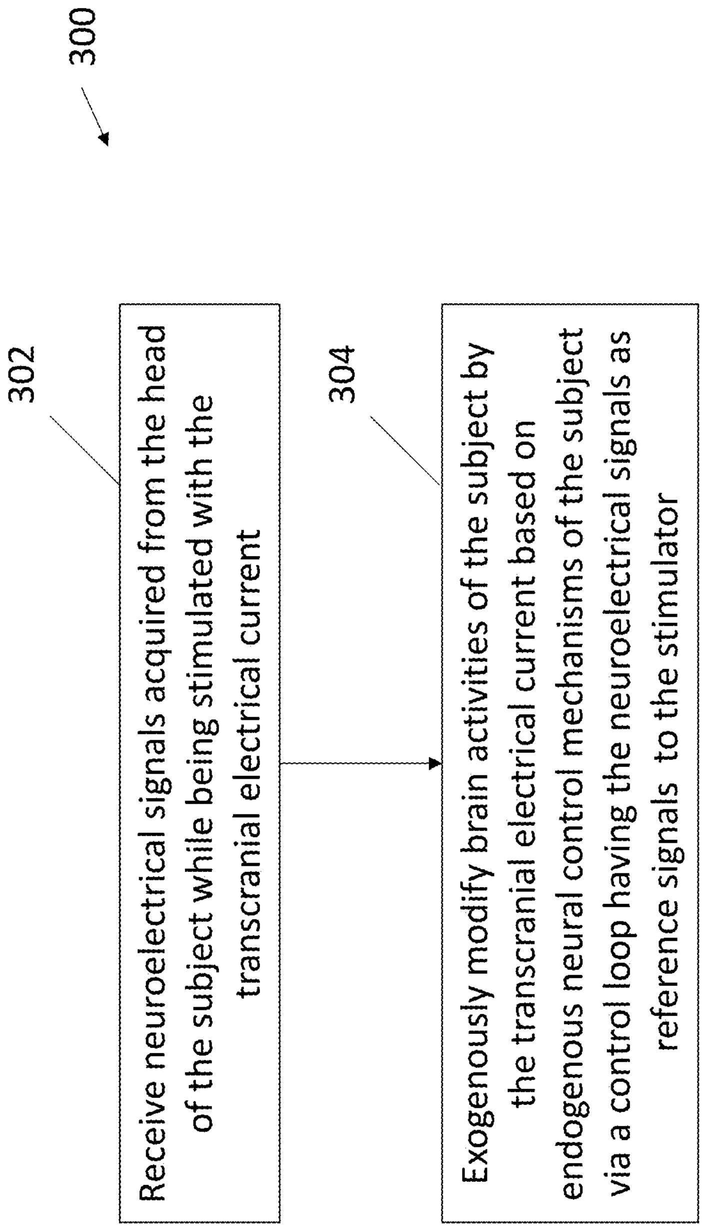
FIG. 3 is a flowchart depicting a method of using the system of FIG. 1.
Figure 4A:
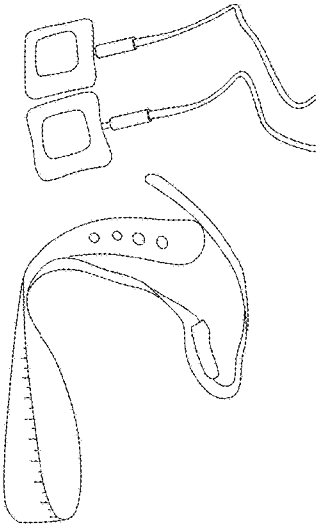
FIG. 4A Prior Art
FIGS. 4A-4D depict different types of tES devices.
Figure 4B:
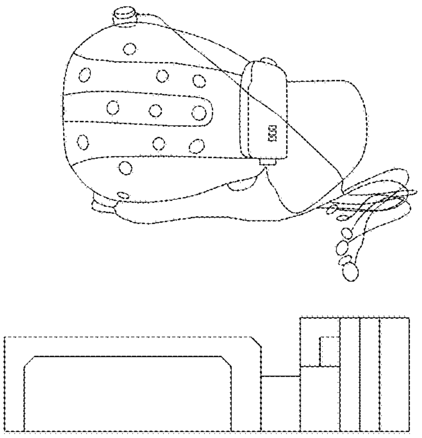
FIG. 4B Prior Art
Figure 4C:
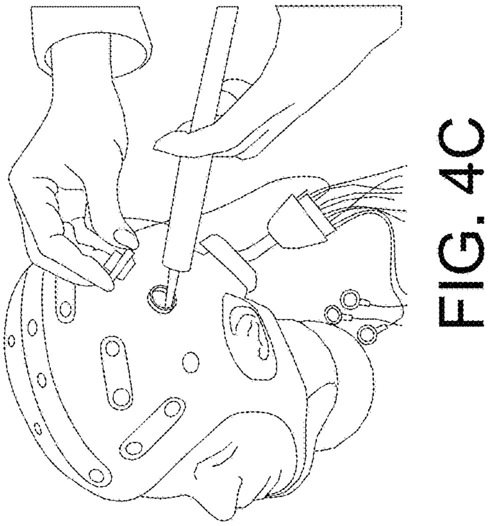
FIG. 4C Prior Art
Figure 4D:
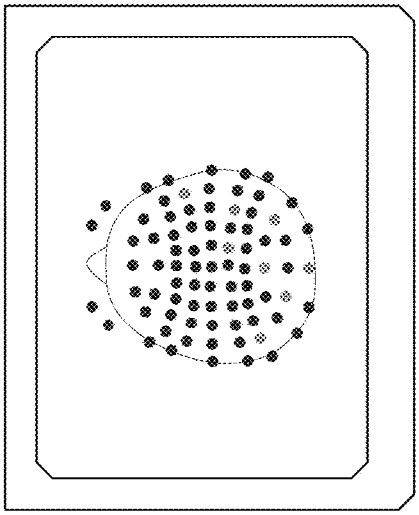
FIG. 4D Prior Art

FIG. 3 is a flow chart of an example method 300 for non-invasive closed-loop tES. Method 300 may be implemented with system 100. In the example embodiment, method 300 includes receiving 302 neuroelectrical signals acquired from the head of the subject while being stimulated with the transcranial electrical current. Method 300 further includes exogenously modifying 304 brain activities of the subject by the transcranial electrical current based on endogenous neural control mechanisms of the subject via a control loop having the neuroelectrical signals as reference signals to the stimulator.

In some embodiments, the method 300 may further include individualizing the transcranial current to the subject based on the magnetoencephalography (MEG) data and/or electroencephalography (EEG) data of the subject. In some embodiments, method 300 may further include individualizing the transcranial current by optimizing an individualized whole-brain model of the subject based on the MEG data and/or the EEG data. The whole-brain model includes directed connectivity between brain regions of the subject and characteristics of each brain region. In some embodiments, method 300 may further include optimizing the individualized whole-brain model based on resting-state EEG data and EEG data acquired when the subject was under tES. In some embodiments, method 300 may further include optimizing optimize the individualized whole-brain model based on a Kalman filter. In some embodiments, method 300 may further include optimizing the transcranial electrical current based on the individualized whole-brain model.

In other embodiments the method 300 further includes measuring a control objective of the transcranial electrical current based on reachability of the endogenous neural control mechanisms. Reachability is defined as a reachable set describing patterns of brain activities obtainable by modulating activities of input nodes. In this embodiment, the method 300 may further including exogenously modifying the brain activities via the control loop by controlling the reachability and/or controlling the reachability by shifting brain activities to optimize the reachability. Further, the method 300 may include controlling the reachability by modifying vector fields of neural states in a brain of the subject. In some embodiments, the reachability may be determined based on the vector fields using a quadratic norm.

EXAMPLES

Example 1

Introduction

An overt point of intersection between control engineering and clinical brain science lies in the development of neurostimulation technologies for modifying brain activity and consequent behavior. Such methods have been in use for many decades for a broad spectrum of neurological and neuropsychiatric illnesses, and have demonstrated high clinical efficacy. However, the invasiveness of some stimulation methods, including electroconvulsive therapy and deep brain stimulation, have limited application to exceptional cases, typically in individuals with very advanced forms of disease. An emerging goal in neurology and psychiatry is the development of methods and technology that can be used in first-line treatments, particularly to address cognitive deficits, such as impairments in attention and memory. Typical first-line clinical strategies, including behavioral and systemic pharmacological interventions are effective with respect to specific symptom clusters (e.g., mood) but are less effective with respect to cognitive effects, though exceptions exist. Moreover, these strategies are often mechanistically opaque and, for unknown reasons, are ineffective in many patients. Thus, a challenge and opportunity exists to extend the synergy between control engineering and clinical brain science to develop principled and interpretable strategies for brain stimulation that can enhance cognitive function in patients and perhaps, eventually, in healthy individuals.

A promising avenue towards the above goal involves use of non-invasive brain stimulation technologies, such as transcranial Electrical Stimulation (tES), which involves applying weak current to the brain using two or more electrodes positioned on the scalp. Most tES devices are current-controlled, to account for variation in skin/skull conductance; the strength of stimulation is therefore described in terms of current (typically 1-4 mA).

Contemporary approaches to tES are (almost always) open-loop in nature, and have taken the form of either (i) DC stimulation (tDCS), theorized to increase/decrease neural excitability or (ii) single-frequency AC stimulation (tACS), theorized to entrain brain activity to the applied sinusoidal signal. These techniques largely share the same motivation: to increase the strength of activity in a brain area (and/or frequency) correlated with a target cognitive function. The efficacy of the approach has been debated and appears to exhibit individual variability, though some early studies indicate intriguing potential for affecting complex brain functions. Current approaches are, however, potentially limiting, since they are largely based on trial-and-error, without directly leveraging the role of brain dynamics in neural computation. Hence, there is a clear opportunity at the nexus of engineering and brain science to develop control-theoretic approaches that can positively impact the utilization of these emerging technologies.

In the present disclosure, we explore the challenges and potential of a control-systems framework for designing controllers to enhance human cognitive function, with a focus on the development of conceptual and mathematical objective functions. The present disclosure identifies current technical and theoretical challenges in human neural control across spatial scales and suggest promising pathways forward. In particular, we focus on the formulation of objectives and system identification paradigms as a precursor to the eventual synthesis of control strategies for brain stimulation.

The present disclosure includes a brief introduction to tES application, followed by a general discussion of the state-space description and theoretical constraints of closed-loop tES. In Section 3 we review previous approaches to brain modeling and control and highlight recent advances in neural system-identification. In Section 4 we critically-review current tES frameworks and argue against their underlying logic. Our novel contribution is a control-theoretic reframing of neurostimulation objectives in Section 5. Lastly, we identify promising pathways and fundamental limitations in using macroscale tES to influence the cellular-computations that underlie cognition (Section 6).

1.1 tES Hardware

Referring to FIG. 4, similar to EEG hardware, tES devices come in three forms: single-channel, multi-channel, and high-density. Single-channel devices typically use two unmounted electrodes and are unique in continuing to support large surface-area electrodes in the form of either "paddles" or saline-soaked sponges. FIG. 4A depicts a single channel device with medium sized sponge electrodes which are attached to the head using an elastic band. These first-generation devices continue to be popular, particularly for DC stimulation. By contrast, multi-channel devices use slightly larger variants of EEG electrodes with contact formed by a small sponge-pedestal or electrolytic gel. The multiple channels afforded by such devices have been used to either concentrate the electric field (e.g. by surrounding a cathode by a ring of anodes) or to stimulate separate parts of the brain. Most recently, high-density devices have been developed in which electrodes are mounted in an EEG-style net/cap. FIG. 4B depicts a reverse view of a high-density device mounted on an adjustable head-cap. This particular device is mobile with the battery/control unit on the back. Referring to FIG. 4C, an electrolytic solution is used to improve contact between the scalp and the electrodes of the device. FIG. 1D depicts a software suite for controlling the device and monitoring impedance (screen shows impedance monitoring used during device setup). These devices are often designed to be used alongside high-density EEG and some integrated systems allow the same electrodes to be assigned either stimulation (tES) or sensing (EEG) roles.

1.2 Previous Attempts at Closing the Loop for tES

As previously mentioned, the preponderance of tES studies have employed open-loop stimulation. However, there has been increasing interest in developing closed-loop brain-stimulation approaches. Several emerging lines of research have begun exploring these avenues with considerable variation in the measurements used to construct feedback. Example approaches include coupling tES and EEG spectrograms and approaches which attempt to empirically maximize stimulation parameters (amplitude, frequency) by measuring their effect on behavior. Other studies have explored synchronizing tACS onset to ongoing EEG measurements (i.e., starting tACS when EEG is at 0-phase). The latter case represents the current state-of-the-art, but has only been explored recently and in a small number of studies such as one concerning the repair of memory function in older adults, and another in which tES was applied during sleep.

1.2.1 Closed-Loop Processing

As discussed above, tES has clearly advanced beyond pure open-loop protocols. However, these advances have largely been driven by heuristics which may be improved upon by formal control-synthesis. For the present, we solely consider the coupling of tES with brain measurements (as opposed to behavior). As with other control-systems, there are several design considerations in establishing closed-loop tES. On the measurement side, neurophysiological effects are often super-imposed with other sources of bioelectricity such as eye movements (the eye is polarized), muscle tension, and cardiac activity. These artifacts are typically removed by Independent Component Analysis (ICA) which is very successful at identifying linear artifacts, such as heart-activity, and easy to implement online as a spatial filter using public software packages. This process is further augmented by regressing out other physiological signals which can be recorded simultaneously (EOG, EMG, ECG, etc.). However, other artifacts, such as motion, may be too large and variable to fully correct online (such timepoints are normally discarded offline).

Timing is also an important consideration for closed-loop design. Unmodeled temporal delays compromise the performance of a closed-loop system and can lead to qualitative changes such as a loss of stability. A significant literature now considers delayed systems, particularly in the context of linear regulators. However, for nonlinear stochastic systems, delays are particularly bothersome. For a deterministic system, model-predictive methods can be used to estimate the system's current state from lagged measurements. In a stochastic system, however, the action of a control signal (δx/δu) will depend upon unknowable disturbances (process noise) that occur during the delay. Minimizing such delays should therefore be considered in the control-design process. Since the lag between a control-command and electrical control-delivery can be made negligible, we focus upon delays generated by computing devices. We note, however, that many commercial tES systems do not allow direct control of the amplifier by external devices which can generate insurmountable lags (i.e., seconds) when using proprietary software.

At rest, human EEG is dominated by fluctuations in the alpha-band (8-12 Hz). In principal, M/EEG data are thus digitized at an adequate rate (typically 250 Hz-2 KHz) to observe this process in real-time. However, additional time is lost during the buffer process and subsequent data processing. Although some of these concerns are related to processing-speed, online digital filters inherently generate output-lags. This feature leads to a fundamental trade-off between filter-order and temporal lag which is not solved by faster hardware. Lastly, significant processing delays can result from the control-algorithm. Brain dynamics are nonlinear, noisy, and high-dimensional. Such features generally necessitate numerical techniques and some algorithms may be too expensive to compute online. For example, solving the Riccati equations associated with a 100-dimensional system can take tens of ms per case, but 100-dimensional matrix inversion is easily performed at several KHz (tested in MATLAB). Thus, control algorithms involving an inverse-Jacobian may be tenable, whereas regulator-style solutions may be too expensive to apply directly. We also note that direct approaches are not always necessary, or recommended. Substantial advances have been made in model-order reduction and statistical/machine-learning approaches to solving control-problems from a parameterized model of the underlying system. We expect that such approaches will prove instrumental in filling this gap.

2. Problem Setting and Constraints

We consider a prototypical tES scenario wherein current is administered at one set of scalp electrodes and brain activity is recorded via another (possibly overlapping) set of scalp electrodes. Due to the low conductance of the skull, a large portion of applied current shunts across the scalp while, conversely, the scalp potentials (e.g., recorded via electroencephalography, EEG) generated by brain activity are relatively weak. Electrical fields primarily derive from/interact with pyramidal neurons, which are oriented approximately normal to the cortical surface, whereas the contribution of non-oriented cells is typically assumed negligible. The temporal resolution of measurement/stimulation is on the order of milliseconds and hence it is reasonable to assume that the dynamics can be well-approximated by a discrete-time system with time-step equal to the sampling resolution. Likewise, a quasistatic approximation of induced electromagnetic fields is justified, so that a model can be written in the form:

$$x_{t+1}=f_t(x_t, Bu_t, \omega_t) \tag{1}$$

$$y_t=Cx_t+\eta_t \text{ for } u_t=0, \text{ else undef.,} \tag{2}$$

in which $f_t$ is a state-transition function, $u_t$ is the applied current (i.e., stimulation), $x_t$ is a vector of neural state variables and B, C denote the control and measurement matrices (gain), respectively. We denote the process and measurement noise as $\omega_t$, $\eta_t$ respectively. For the present purposes, we do not require any assumptions (e.g., independence) for $\omega_t$, $\eta_t$. This framing describes a closed system in the absence of stimulation. In reality, the brain is not a closed system, hence an extension of $\omega_t$ to include sensory input may also be useful (in which case $\omega_t$ will be autocorrelated). Often, in practice, the influence of $\omega_t$ is modeled as additive.

2.2 Constraints on tES as a Control System

Despite the potential of the above modeling paradigm, several nontrivial challenges for identification and control permeate this setup. First are basic but important pragmatic issues surrounding tES technology. Since stimulation saturates recording electrodes (a phenomenon known as stimulation artifact), generic instantaneous-feedback approaches are technically impractical. Similarly, this issue presents a potential challenge to identifying input-output system models. The latter is compounded because only a limited amount of stimulation data can be collected from humans, on account of both safety constraints and practical issues such as maximum amount of time individuals can maintain attention while engaged with a stimulation apparatus.

Further, the measurement process involves both spatial mixing of measured outputs (from the different neural generators/brain regions) and a latent-variable problem as the majority of state-variables (other cell-types, subcortex, molecular mechanisms etc.) are not directly measurable. This results in a challenging dual-estimation problem for identification (i.e., unknown state and parameter values) as well as state-estimation (e.g. filtering problem) for closed-loop control design. Together, these constraints provide significant challenges for black-box identification/control paradigms.

2.3 Limitations of Identification-Free Frameworks

Due to this complexity, a natural question is whether system-identification is truly necessary. Control approaches that do not require explicit system identification have been used in neuroscience and typically involve tuning a prototype control module, e.g., PID, based upon input-output experiments. Such approaches have previously been employed in other neuroscience applications. At the cellular-level, identification-free feedback control of single-cells has been a staple of neurophysiology for the past century: the voltage clamp, current clamp, patch-clamp etc. techniques. Feedback control has also been applied to controlling the firing rate of neurons using PID designs. However, a common feature of these identification-free scenarios is that: (a) they are amenable to tuning a small number of feedback-control parameters and, (b) the control objectives are fully defined by measurements (i.e., a neuron's membrane potential) as opposed to latent variables (i.e., an underlying neural 'code' or unmeasured state-variables). Moreover, controls of this class are generally designed within a linear range of operation and are tolerant of input constraints. By contrast, human brain stimulation at the whole-brain scale involves strong input constraints. Current technical constraints also prevent continuous real-time feedback control due to the previously-mentioned inability to (noninvasively) measure and stimulate the brain at the same time. These features further suggest that a challenging system-identification stage is necessary for control.

2.4 the Difficulty of Formalizing Cognitive Enhancement as a Control Objective

More significantly, neurostimulation faces ambiguity in the formulation of control objectives. Whereas the framing of objectives is comparatively straight-forward in other control domains (e.g., tracking, disturbance rejection, etc.), the ultimate objective of neurostimulation is cognitive enhancement or, more generally, altering some aspect of cognitive processing as reflected in human behavior. Framing these objectives in quantifiable state-space formulations is nontrivial due, in part, to the abstractness of the problem. In particular, there is an obvious but formidable distinction between a motor-output (e.g. pressing a button) and the set of neural computations which led to this output. Whereas the former may have a straightforward conceptualization in terms of state-space targets (exciting the relevant portions of motor-cortex), the latter describes a mapping from the cognitive-task context onto the appropriate responses. In this context, there are two inputs to the system: the task environment and electrical stimulation.

From this perspective, the functional significance of neurostimulation is to imbue favorable properties to the vector-field that support the implementation of a given computation (i.e., produce the correct response given environmental input). Therefore, we propose that the objective of neurostimulation should be to alter the brain's control properties such that environmental 'inputs' will produce brain activity that will push the system towards the correct output. Such a concept is distinct from imposing a prescribed pattern of activity determined a priori. We proceed to formalize these notions with an emphasis upon altering input-output relationships and control properties, including reachability, within relevant brain circuits and areas.

Figure 5A:
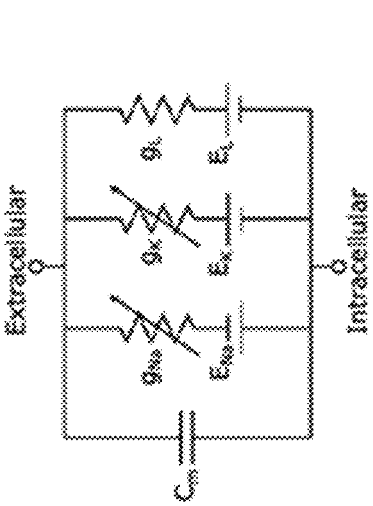
FIGS. 5A-5D depict levels of modeling in neuroscience.
Figure 5B:
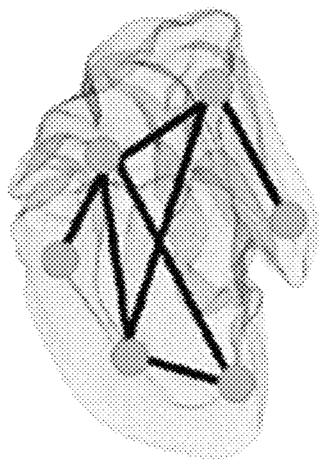

3.0 Controlling Models of Brain Dynamics 3.1 Modeling and Control at the Cellular Scale FIGS. 5A-5D depict levels of modeling in neuroscience. The traditional control design can be classified as being either based upon a model of the underlying system, or using model-free approaches. As in other sciences, models have a long history in neurophysiology, with some of the earliest models, Hodgkin-Huxley and the cable theory, continuing to be used in cutting-edge research. FIG. 5A depicts the cellular Hodgkin-Huxley model which accurately describes the major currents that impact neural membranes. These models are currently viewed as deriving from biophysical first-principles, although the Hodgkin-Huxley equations were originally derived through system-identification. These models, coupled with later descriptions of other voltage-gated channels, give highly accurate predictions for many single-cell phenomena. Significant attention has been directed at analysis and control of neural activity at this spatial scale, including work describing control strategies for one or more Hodgkin-Huxley model neurons and controlling the timing and patterning of spiking activity. Reduced forms of these models have been used for real-world control of brain cells.

3.2 Large-Scale (Whole-Brain) Modeling Frameworks

At the whole-brain scale, such canonical models do not yet exist. The closest analogues, in this case, consist of 'neural-mass' and neural-field models in which mean-field approximations are used to reduce all of the neurons within a brain region into a single state-variable per cell-type, shown in FIG. 5B. These black-box models typically employ artificial neural networks, including combinations of convolutional "encoding" layers (CNN) and recurrent networks (RNN) to generate dynamics. These models are sometimes coupled with additional population-average molecular/channel dynamics. These models often take one of two forms:

$$x_{t+1}=W\Psi(x_t)+g(x_t)+\omega_t;\ \text{or} \tag{3}$$

$$x_{t+1}=f(x_t)\Psi(Wx_t)+g(x_t)+\omega_t. \tag{4}$$

The first form models $x_t$ as a voltage-type variable which is transformed into neuronal "spiking" via the activation function. Neuronal "spiking" is multiplied by connection matrix W and local dynamics are represented by g. In the latter form $x_t$ directly represents the neuronal "spiking" (i.e., $x_t$ in Eq. (4) is analogous to $\Psi(x_t)$ in Eq. (3)), so the activation function $\Psi$ is applied after multiplication by W. The optional function $f$ applies state-dependent gain. All indicated functions ($f$, $\Psi$, g) are "stacks" of univariate functions (i.e. $\delta f_i(x)/\delta x_{j\neq i}=0$). Some variants of these models also include lags, although their necessity is unknown.

Previous work has concerned controlling these models in small networks (sub-circuits of the brain), including applications in epilepsy and motor disorders, primarily in Parkinson's Disease. In these applications, model parameters are typically borrowed from previous anatomical and neurophysiological studies.

The analogous whole-brain models also use prior literature to parameterize the internal dynamics of each brain region, while the connection strengths between brain regions are often assumed to be proportional to the number/volume of connections (white-matter) between brain regions. These models have achieved some successes in reproducing long-term statistics that are characteristic of brain activity (power spectrum or covariance between brain regions).

However, the development of models that forecast or predict neural activity trajectories at whole-brain scales without identification (e.g., using white matter connectivity) remains an elusive goal. Clearly, such capability to approximate well the underlying vector fields is an important precursor to model-based control synthesis. Indeed, while some control-strategies derived from existing models may prove useful, significant concerns may arise regarding the accuracy of the ensuing vector fields, and consequently could undermine confidence in the reliability of the synthesized solution as well. As such, there is an unmet need for methods to identify large-scale brain models accurately from brain-activity recordings.

3.3 Specifying Modeling and Identification for Whole-Brain Dynamics

Neural systems identification methods can be grouped into black-box and grey-box frameworks. These approaches differ in that black-box models emphasize predictive power (in terms of measurements) whereas grey-box models must balance prediction power with interpretability and model-complexity. From a scientific standpoint, one advantage of grey-box models is the ability to interpret system parameters for basic scientific inferences. For the current discussion, however, we limit our comparison to their potential efficacy for whole-brain control. By 'grey-box' model we will refer to model forms with parameters that are explicitly driven by physiology. To make this distinction concrete, we will consider models to be grey-box if at least some of the model parameters (known or unknown) have units other than Hz (i.e., they represent physical or physiological quantities). Importantly, our description of a model as 'black-box' does not imply that it is physically uninterpretable, and we begin with a brief review of such techniques.

3.3.1. Black-Box System Identification

Figure 5C:
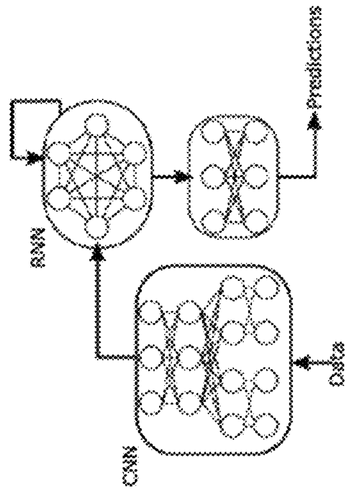

To organize our discussion of black-box models in neuroscience, we consider three classes: machine-learning, input-output models, and statistical descriptions (e.g., autoregressive models). As in other fields, machine learning approaches for neuroscience are developing rapidly and are dominated by artificial neural networks. Referring to FIG. 5C, whole-brain "neural mass" models describe macroscale (as opposed to cellular) brain activity. Brain connections are typically parameterized from diffusion imaging data which can estimate the amount of wiring between regions, not direction or sign of influence. Circles indicate different brain regions. These approaches have been used for latent factor identification and to forecast future brain activity patterns, e.g., predicting epileptic seizures. Input-output characterizations include the calculation of transfer-functions using electrical stimulation, such as in the estimation of phase-response curves to analyze and design control of individual neurons. Statistical models (which can also involve input-output descriptions), involving one or more autoregressive terms, have been used for state-estimation with EEG and fMRI data among other applications.

Black-box models are also useful in predicting nonstationary phenomena such as changes in spectral power or synchronization patterns. Successful applications in this domain typically use optimization methods and include the prediction of changes in (region-specific) spectral power and seizure components from EEG data. Due to the long timescales involved, the timing and nature of these phenomena are difficult to predict online using state-space methods (e.g., forward simulation). They may also involve slower molecular mechanisms or other physiological details that are excluded from state-space brain models, such as neural mass models.

In contrast to neural networks, statistical "black-box" models are easy to interrogate and flexible in terms of how "states" are defined. Hidden Markov Models, for instance, are a class of unsupervised models in which the underlying system obeys a discrete Markov process. Such frameworks are intriguing as they often deal with temporally-extended states which could be defined in the spectral domain or in terms of (auto)covariance. As such, they are amenable to predicting the probable long-term outcomes of moving the brain into such a state. However, since these models do not operate in state-space they cannot predict de-novo how control signals interact with the system dynamics. As such, HMMs may be useful for considering multiple timescales in the control objective, but cannot, by themselves, identify tES control solutions.

Moreover, from the standpoint of control design, there are key considerations with respect to generalizability of black-box models, and in terms of their compatibility with pertinent control objectives. In considering the generalizability of black-box models, we do not refer to whether the model is over/underfit with respect to the training-data's domain (which can be assessed via cross-validation). Rather, we refer to the ability of a given model (fit to a subject's output-only data) to describe the brain's vector-field in novel regions of state-space. This aspect may be especially important if the objective is to steer brain activity from a pathological state or regime, to one that is benign. In some cases (e.g., epilepsy), patients may be theorized to switch between pathological and non-pathological dynamical regimes. In this case, data may be available for the target state-space regions, although a designed controller may nonetheless steer activity through an unnatural and hence novel region of the state space in attempting to reach the previously-observed non-pathological regime. On the other hand, degenerative brain disorders result in a more persistent pathology so data in the 'target' state-space regions may be unavailable. In this case, grey-box models which were less accurate in describing the baseline regions of state-space may still outperform black-box methods in generalizing to novel regions of state-space, purely by virtue of their physiological constraints and interpretability.

Lastly, black-box methods are inherently tied to the measurement-space. In other words, for the measurement matrix C (as in Eq. (1)) the state-space models of such systems are restricted to the form:

$$z_{t+1}=f(z_t);\ z_t\in\text{span}(C),\ \forall_t \tag{5}$$

as opposed to engaging with the full state-space as in Eq. (1). This aspect means that it is harder to treat objectives that are not defined in the measurement space, such as those featuring latent state variables or properties of the underlying vector-field. In Sections 4 and 5 we proceed to discuss such objectives in more detail and describe their potential importance for emerging applications in brain stimulation for cognitive enhancement.

3.3.2. Grey-Box Models and Numerical Advances

Figure 5D:
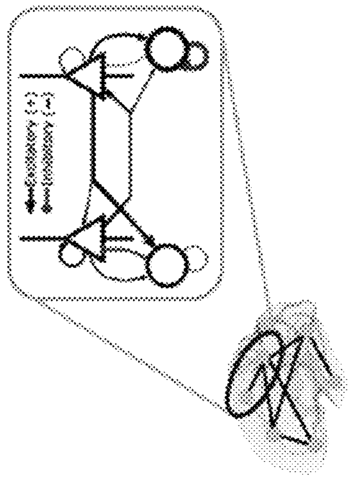

Grey-box system identification methods have a long history in cellular neuroscience, starting with the aforementioned work of Hodgkin and Huxley using input-output identification on the squid giant axon. Current efforts in cellular grey-box identification emphasize joint-estimation, typically with only the membrane voltage or firing rate directly measurable. Grey-box identification has also been performed with small network models and in larger-scale brain models. In the latter case, efforts have been divided into approaches which seek to refine parameterized models and those which perform identification with little or no assumptions outside of a general mathematical form. In the former case, neural-mass models have had a very small set of parameters tuned in order to better replicate long-term statistics such as correlation patterns. However, since these models are fit to long-term statistics, as opposed to directly forecasting brain activity, it is not yet clear whether they are sufficiently accurate for control synthesis, particularly over short timescales. Other approaches, however, have been developed to fit single-subject brain models directly to brain activity using neuroimaging data (fMRI, EEG, MEG, etc.). Referring to FIG. 5D, an exemplary grey-box model is depicted. Grey-box models leverage brain-activity time series to directly parameterize detailed, mechanistic models of local brain circuitry and brain connections (including direction/sign). FIG. 5D shows the microcircuitry model used, which models the interaction of pyramidal cells (triangles) and interneurons (circles). Dynamic Causal Modeling (DCM) is a prominent case of using Bayesian methods for the latter approach. DCM models consist of linear state-space models for fMRI, while faster-timescale data (MEG and EEG) is estimated using a linear approximation of an underlying nonlinear neural-mass model. The DCM methodology is an example of joint-estimation for latent variables in that DCM models estimate latent neural activity from fMRI data and the activity of non-pyramidal cell-types from EEG data (which primarily derives from pyramidal cells).

A limitation of the existing DCM methodology, however, has been high computational complexity which has limited its ability to scale to whole brain models, although this barrier has been recently reduced under assumptions of linearity in the dynamics. For models with high temporal resolution, however, analyses have been limited to a small number of brain regions (usually less than 10) with the assumption that spatially-localized (source-level) signals are available (i.e., it does not directly treat the issue of spatial mixing). To bridge this gap, our group has recently developed a number of techniques for highly-scalable joint-estimation of neural systems (i.e., unknown states and parameters). These include the ability to quickly estimate high-dimensional (419) brain models (which take the form of Eq. (3)) using output-only fMRI data and to identify environmental and endogenous drivers of brain activity as reflected in fMR. Most recently, however, we have developed a general, scalable framework for joint-estimation that also treats the issue of signal-mixing via a Kalman-Filtering technique. This advance has enabled us to estimate whole-brain neural-mass models (100 regions×2 cell-types) directly from single-subject MEG data (shown in FIG. 5D). We anticipate that these advances in systems identification will facilitate corresponding improvements in neurocontrol technology.

4. Current Frameworks for Brain Stimulation and their Limitations

Traditional control objectives include control-to-point/set, tracking, stabilization, and synchronization, potentially including additional penalties (minimum energy, time etc.). By contrast, the formulation of objectives for human brain stimulation is less straightforward. While the desired outcomes can be concisely described in terms of psychological constructs (e.g., improving working memory) and quantified in terms of behavior (maximize the number of items that can be recalled from a list with some level of accuracy) formulations in terms of brain activity are more challenging. A key feature of this problem is that while noninvasive brain stimulation induces anatomically broad effects (relative to sub-millimeter micro-circuitry), the neuronal microcircuits underlying a given computation are often spatially diffuse and less well understood. Linking these scales formally results in a control-problem of the form:

$$\hat{x}_{t+1}=f(\hat{x}_t, V^T, Bu_t, \omega_t) \quad (6)$$

$$y_t=CV\hat{x}_t+\eta_t \quad (7)$$

in which the matrix V adds together the contribution of cells ($x_1$) in each brain area (i.e., $x_t=V\hat{x}_t$), while the macroscale matrices C, B are the same as in Eq. (1). The symmetries generated by V obviously impede treatment of the underlying microscale system $\hat{x}$ by macroscale controller $u_t$.

4.1. Case Study I: Random Dot Motion

4.1.1. Increasing Activity is not Sufficient to Augment Performance

This mismatch has significant impact on how objectives should be defined. To illustrate this point, consider a popular test of perceptual decision making: the Random Dot Motion task. In this task, subjects are visually presented with a patch of particles/dots moving according to a random walk with slight drift in one direction (i.e., the dots' motion is mostly random, but weighted towards one direction). Subjects must decide which of two options (e.g., left/right) is the correct direction. Empirical and computational studies of this task have converged around a model in which each option (direction) is represented by a particular set of neurons which integrate noisy input ('evidence') elicited by objects moving in that direction. The subject's decision corresponds to the first option (direction) to pass a threshold level of activity (the phenomenology of such integration is often modeled as an Ornstein-Uhlenbeck, or drift-diffusion, process).

Under a conventional tDCS perspective, the stimulation objective should be to increase the brain activity within that region since gross neural activity in the region (which contains the neurons for all directional choices) increases when performing the task. However, the model predicts that when the input to both options (neuronal populations) is increased, decisions will be faster but less accurate (the speed-accuracy tradeoff). Thus, direct-current stimulation is not predicted to enhance the subject's perceptual decision making per se, but rather effects would be expected to alter the degree to which they weight speed vs. accuracy in making a decision (which can already be accomplished by telling the subjects to wait longer/shorter). Analogous arguments can be made for other brain circuits. Thus, we argue that increasing neural excitability within a given brain area is not, in general, a sufficient strategy to improve cognition. This is not to say that direct-current stimulation is totally ineffective, as it may produce desirable effects related to increases in the spread/duration of neuronal activity or promoting synaptic plasticity (learning). However, the key point is that some cognitive functions may require a more nuanced objective formulation.

4.2. Using Dynamic Stimulation to Modify Information Propagation

A natural alternative to tDCS is tACS which instead uses alternating current (typically sinusoidal). The objective of tACS stimulation is to increase the amplitude of a particular frequency band in the targeted brain area or to entrain neural activity to a desired phase, such as synchronizing two regions. There are many theories regarding the role of neural oscillations in computation. One premise is that brain oscillations act as carrier waves. In this regard, information is transmitted via phase, amplitude, frequency-modulation or, in other scenarios, by the relationship between different frequency-bands or between the macroscale oscillations and cellular ('spiking') inputs. These mechanisms selectively engage micro-circuits which are especially resonant to the oscillation frequency or to the phase-offset (delay) between events (e.g., the crest/trough of inputs from different sources). Under this framework, AC stimulation is thought to act by increasing the oscillation's signal strength without modifying the information it conveys, such as by increasing the amplitude of a reference wave when information is coded by phase-coupling. Returning to the Random Dot Motion task (see previous section), a recent study found that participant's accuracy increases when stimulated at 10 Hz (the dominant frequency in visual areas), which is interpreted as increasing the quality of information sent to decision making circuits, since non-selectively increasing signal strength (or quantity) would decrease accuracy (see previous section).

Multiple studies have indicated that tACS can be efficacious in partially restoring cognitive function when applied in a personalized, phase-locked manner. An especially impressive study, by Reinhart and colleagues, demonstrated that memory performance in older adults could be improved to levels comparable to younger counterparts by employing theta-frequency (i.e., 7-10 Hz) tACS phase-locked to brain activity. This study further indicated that applying tACS in an individualized manner, at each subject's spontaneous peak-frequency, further increased the magnitude of neural effects. However, despite these successes, there are several theoretical reasons to believe that these results could be further improved. Recent tACS studies, such as the aforementioned, have demonstrated significant potential to partially restore function in under-performing groups, which have been characterized by altered frequency-domain properties. However, the comparatively weak evidence for improvement in healthy subjects may imply that tACS methods primarily serve to restore de-graded features of signal transmission (e.g., carrier/reference signals) rather than improving the brain's ability to operate upon these features. This approach is also based upon the assumption that sinusoidal stimulation does not alter the content of signals. This assumption is likely violated if information is coded in signal frequency. Likewise, when information is coded in signal phase, this assumption requires that the stimulation input does not alter the phase (which explains the advantage of phase-dependent stimulation). More generally, these stimulation frameworks are based on neural computation models in which temporal dynamics are used to encode/decode information as it is propagated between brain areas, but does not enable a general framework in which neural dynamics are the underlying mechanism of computation.

5. An Example of Formulating Control-Theoretic Objectives

We now explore the potential of control-theoretic methods to re-formulate the optimization objective. Our framing involves a change of viewpoint to emphasize facilitating the endogenous ability of the brain to reach target cognitive states as opposed to forcing the brain along a particular time-varying trajectory. In other words, we propose an approach to exogenously modifying brain activity that is premised on leveraging endogenous neural control mechanisms.

5.1. Case Study II: Stroop Task

5.1.1. Lessons from Endogenous Control Mechanisms

In neuroscience and psychology, 'cognitive control' refers to the diverse set of processes that modify human behavior based upon the environmental context and goals. Impairment of cognitive control is a core component of many psychiatric disorders. Prominent theories of cognitive control stress its modulatory role in determining how information is processed, interacts with internal states, and affects actions. This ability is thought to be accomplished by altering how the brain interacts with inputs from the periphery. Brain regions (e.g., prefrontal cortex, PFC), which maintain rule representations, are believed to proactively bias the neural pathways along which information flows.

Figure 6A:
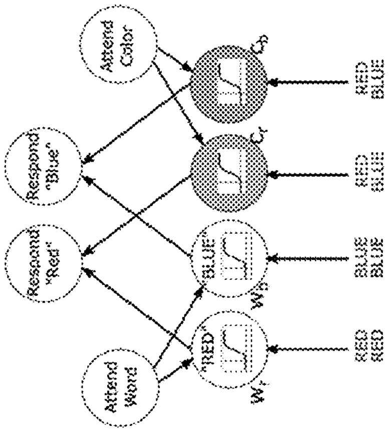
FIGS. 6A-6C depict examples of the Stroop Task.
Figure 6B:
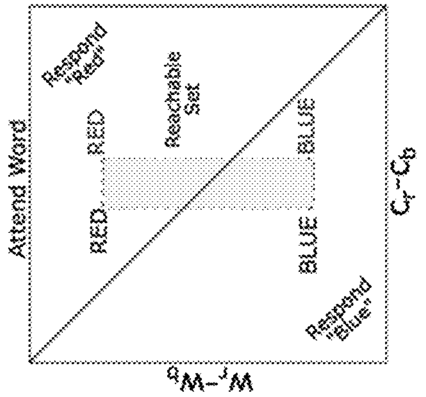
Figure 6C:
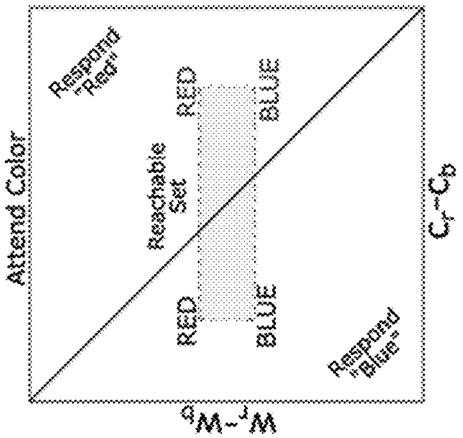

The above theory has been used to develop neural network models of classic cognitive tasks such as the Stroop Task, in which subjects are asked to report either the ink-color or word of colored text (e.g., 'Red' in blue font; see FIG. 6A). Task instructions (attend to work vs. color) promote specific pathways through which input propagate. Over short timescales, these instructions are believed to be maintained in a stable 'read-only' state associated with the modulatory neurotransmitter Dopamine. When the current behavioral strategy is ineffective, neural activity in PFC is thought to destabilize, enabling new information to be encoded. Once an effective approach is found, PFC dynamics stabilize around this activity pattern, thereby storing the associated behavioral strategy. More generally, brain activity has been found to stabilize along a more limited set of patterns in response to sensory stimuli and cognitive tasks. These conceptual models suggest an alternative route towards cognitive enhancement. Rather than altering the frequency-profile of brain activity, a framework emerges that seeks to modulate how environmental inputs interact with the brain by altering the stability properties and reachable-sets of local brain dynamics. FIG. 6B depicts activation of the latent "attend word" state shapes the reachable set so that the response-boundary separates inputs by word. FIG. 6C depicts an analogous figure for the "attend color" condition.

5.2. Case Study III: The Attentional Blink

5.2.1. Relevant Control-Theoretic Measures

There are thus two levels to the control problem: first identifying the local control properties that are advantageous to cognition and then designing a stimulation protocol that will (locally) promote these properties on the augmented stimulator-brain system. To be concrete, we will present these issues in terms of another well-studied cognitive task and phenomenon: the attentional blink.

The 'attentional blink' refers to the fact that when two visual images are rapidly presented in sequence (200-500 ms delay between images presented for 100 ms each), most subjects (>50%) are unable to report the second image. Interestingly, this effect is non-monotonic, as subjects can process both stimuli for extremely short delays (e.g., 100 ms) and subconscious traces of information present in the second image (e.g., the meaning of word images) are evident in later behavior. These effects suggest that the attentional blink reflects changes in the system's (i.e., the brain's) internal states as opposed to limitations in the processing-speed for visual input.

From a stimulation design perspective, we are interested in how a control paradigm could be designed to eliminate or attenuate the attentional blink, as a means to improve visual attention. In this regard, several attempts have been made to attenuate the attentional blink using DC brain stimulation, yet with inconsistent findings. Limited prior study is currently available concerning AC stimulation. We hypothesize that the attentional blink and similar cognitive bottlenecks manifest changes in the brain's local reachability properties for visual input. More mathematically, for an initial state-space condition $x_0$, a class of admissible control-inputs (i.e., sensory stimuli) $\mathcal{U}$, and a realization of the noise-process $\omega_t$, we define the horizon reachable set as a set-valued function of the initial condition $x_0$ and random process noise $\omega_t$:

$$\mathcal{R}(f, x_0, \omega_t, \mathcal{U}) := \bigcup_{v_i \in \mathcal{U}} \phi_f(x_0, \omega_t, v_i, k) \tag{8}$$

Here, $\phi$ denotes the evolution function for vector field $f$, which could be formulated in continuous or discrete time. As a deterministic function of the process $\omega_t$, the reachable-set given $\omega_t$ is well-defined, even if the distribution of all $\mathcal{R}$ is unbounded due to an unbounded distribution of $\omega$. Returning to the attentional-blink example, we propose formalizing brain sensitivity to incoming visual information using the 'size' of the reachable space according to a quantity, denoted μ, which captures biases in the vector field toward movement in task-relevant directions (e.g., measuring the degree to which the second image can elicit responses in visual brain areas). Direct measures based upon well-established geometric nonlinear control analyses are natural here, but bring about concerns of analytical or computational tractability for high dimensional models. Indeed, reachability and similar control-theoretic assessments are exceptionally challenging, particularly in the presence of multiple inputs. Several metrics have been developed for linear systems, which can be applied to infer properties of linear whole-brain models, including structural brain networks. Such approaches could potentially be used in a state-dependent manner to perform local reachability estimates for nonlinear systems in the vicinity of an attractor under sufficiently weak input and short control horizons. We later discuss more general techniques (see Section 5.3).

For non-local characterizations, however, the reachable set is not convex, and admits multiple ways to describe its breadth. However, a simple description of the reachable set may still be attainable via a metric induced by a quadratic form (i.e., $\mu[X]=\mu_L[AX]$ for a matrix A and the Lebesgue metric $\mu_L$) with the corresponding objective to minimize/maximize $\mathbb{E}_\omega[\mu(\mathcal{R}(x_0, \omega, \mathcal{U}))]$. By a quadratic-norm we are only referring to how the "size" of a reachable set is measured as opposed to implying a quadratic (e.g., ellipsoidal) approximation of the reachable set.

The matrix A should be constructed to have large singular-values in directions in which movement is desirable and small singular-values for directions which contribute noise (or, alternatively, subtract reachability in these directions). Changes in neural activity within the default-mode network, for instance, are associated with mind-wandering, so one construction of the A matrix for the attentional blink would be to have heavily weighted singular-vectors spanning visual-attention pathways, and weakly-weighted (right) singular vectors spanning state-coordinates associated with the default-mode network. This would allow measurement of whether the second image is able to deferentially induce representations in task-relevant (i.e., visual) vs. irrelevant (i.e., DMN) areas. In our formulation, the matrix A is specified a-priori based upon existing knowledge of the underlying neuroanatomy. Another option may be to refine pre-existing assumptions on A based upon which directions are easiest to reach in-practice using an empirical estimate of the Gramian. The empirical Gramian can be useful in identifying directions which are (effectively) inaccessible, in which case they should be removed from A.

The reachable set also depends upon the space of admissible controls ($\mathcal{U}$). For example, only a small subset of potential sensory input signals to visual cortex are likely. Further study will be needed to identify this set. How-ever, a preliminary estimate for $\mathcal{U}$ could be formed via a linear-in-control assumption with corresponding bounds ([a,b]) on input, i.e., mathematically, $$\mathcal{U}:=\{Mv(t)|v_i:[0,k]\rightarrow[a_i,b_i]\} \tag{9}$$

We note that the control matrix for modeling endogeneous control (M) is not, in general, the same matrix used for exogenous control (denoted in Eq. (1)). In the case that the exogeneous ($u_t$) and endogeneous ($v_t\in\mathcal{U}$) controls add, the reachability-optimal control u is the (constrained) solution to:

$$\arg\max_{u\sigma\mathcal{F}_y}\mathbb{E}[\|A[\mathcal{R}_f(x_0, \omega_t, Bu+M\{v\})\|_2] \tag{10}$$

with M{v} denoting the set of admissible endogenous inputs and $u\sigma\mathcal{F}_y$ indicating that the control-solution can, potentially, be a policy on the filtration of y (i.e., past measurements). Importantly, because reachability properties depend upon a model of the brain as a control-system, these objectives are inherently causal in nature: they require specification of which neural populations are the subject of endogenous/environmental control and how changes in their activity under such control relates to cognition. As such, reachability-based control objectives are specific to the cognitive function being targeted and likely involve trade-offs such that there is likely not a universal reachability objective that benefits all aspects of cognition.

5.3. Identifying Reachable Sets for Brain Dynamic Models

As alluded to above, for a general nonlinear control system, the calculation of finite-time reachable sets is highly nontrivial, although a growing number of numerical techniques and freely-available tool-boxes offer some potential for relevant approximations. When no assumptions are placed upon the system vector field, numerical methods typically need to simulate a very large number of potential inputs to estimate the reachable set or using iterated geometric methods, such as zonotope-based analyses.

Fortunately, canonical models of macroscale neural activity generally feature monotone relations (e.g., a region's output is a bounded, monotone function of its current state), which enable much more efficient approaches such as mixed-monotonicity algorithms. A primary challenge in computing reachable sets is the ability to efficiently represent non-convex sets, particularly those which are not simply-connected. These considerations are important for the reachability analysis of neural systems which often generate limit-cycles or quasi-periodic attractors that under small control perturbations generate infinite-horizon reachable sets that are not simply-connected.

Mutual competition is a fundamental principle of the nervous system which promotes winner-take-all dynamics. This feature generates a large number of hyperbolic fixed points, which correspond to when competing populations are perfectly balanced, and the associated unstable manifolds that arise under these conditions. This case brings an important consideration as to whether reachable sets for the brain's internal control laws should take into account the natural imprecision of biological systems. Whereas the analytic reachable set in this case may be topologically-connected (e.g., by traversing an unstable manifold), a small deviation from this manifold could be impossible to later correct with a bounded, delayed control signal. As a result, the set of achievable outcomes, in practice, would be disconnected and significantly smaller than the reachable set. Further study is therefore needed to explicate the properties of endogenous brain control, and exogenous control design may benefit from further development in the theory of reachable sets that consider issues of robustness and uncertainty in constraining the set of admissible endogenous controls.

5.4. Potential Control Strategies for Reachability Properties

Figure 7A:
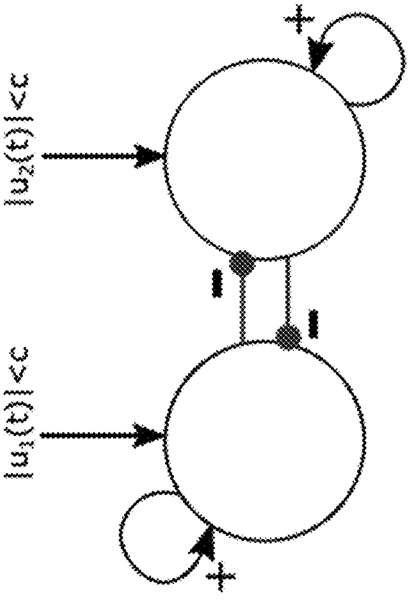
FIGS. 7A-7C depict illustrations of state-dependent reachability.
Figure 7B:
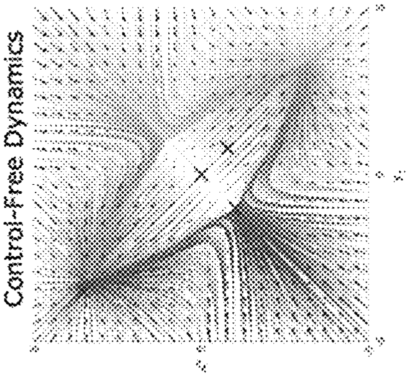
Figure 7C:
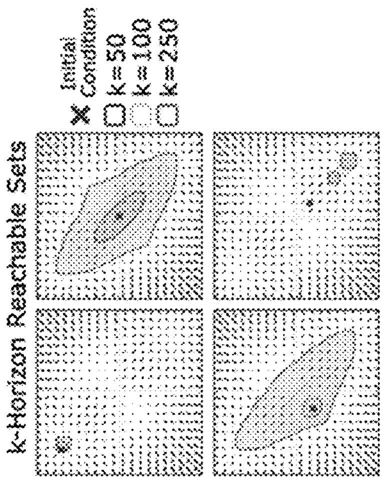

The second level of formulation is designing the exogenous controller with the aim of modifying (and optimizing)

reachability properties for endogenous control. We postulate two pathways in this regard: either (i) by preemptively shifting brain activity to a desirable point/set in the state space, or (ii) by altering the vector field itself. The first case corresponds to an boundary value type problem, but with a new criterion being used to define the desired state (i.e., the state that optimizes reachability properties). FIGS. 7A-7C depict illustrations of state-dependent reachability. Referring to FIG. 7A, a schematic of a recurrent two neuron network is shown with self-excitation, reciprocal inhibition, and two independent, bounded inputs. FIG. 7B depicts an uncontrolled vector field and integral curves (color=initial condition for each curve). FIG. 7C depicts approximate reachable sets for different initial conditions and time-steps (horizons). Note the strong dependence of initial condition and that reachable sets are larger when starting near a separatrix (e.g., top right) than a fixed point (e.g., top left). Future work will be needed to determine efficient means of performing the reachability optimization, although naïve first estimates may be possible by assuming that endogenous inputs are sufficiently small to admit local (time-varying) linearization about the uncontrolled orbits. This assumption would lead to an optimization problem in terms of the sequence of Jacobians (maximizing/minimizing the rate of expansion along certain directions).

Figure 8A:
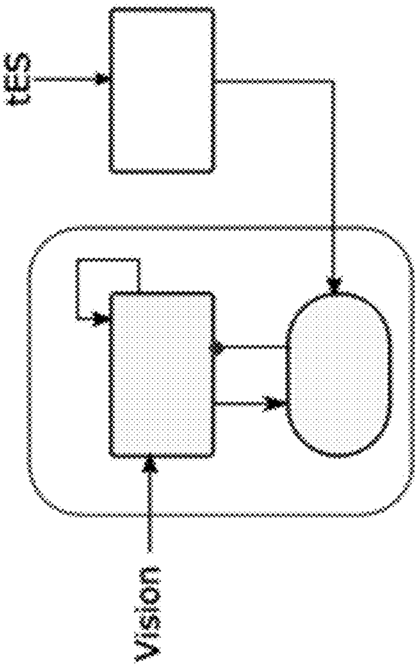
FIGS. 8A-8F depict schematics for controlling computation-relevant (microscale) reachability via macroscale simulation.
Figure 8B:
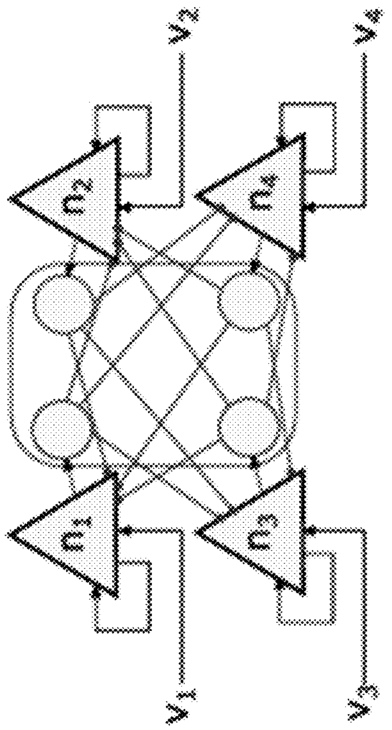
Figure 8D:
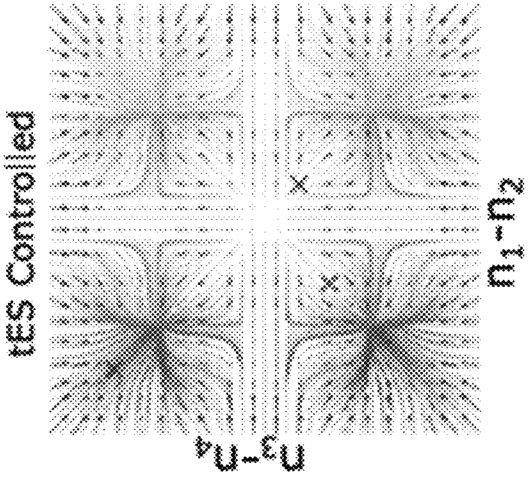
Figure 8C:
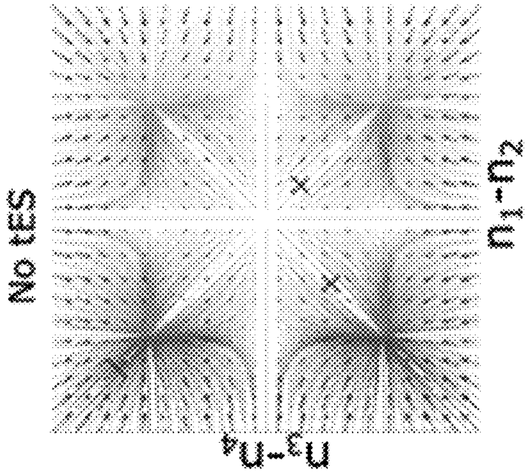
Figure 8E:
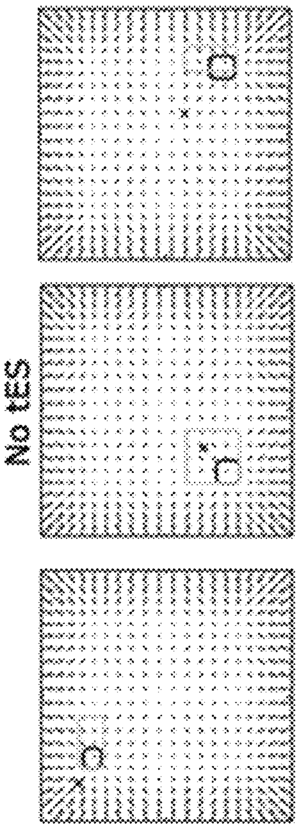
Figure 8F:
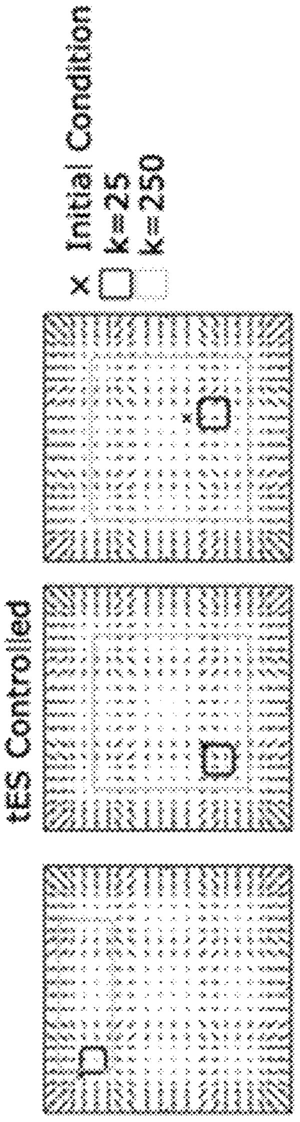

An alternative to this approach is modifying the brain's vector-field, which has more in common with stabilization techniques. Referring to FIG. 8, schematics for controlling computation-relevant (microscale) reachability via macroscale simulation are shown. This pathway is potentially more interesting as it allows switching the reachability objectives mid-task, such as shifting between periods of high reachability (flexible brain activity) and low reachability (more robust activity. FIG. 8A shows a macroscale system schematic. Visual input enters a brain region containing excitatory (green) and inhibitory (blue) neurons. Electrical stimulation (tES) is applied to a separate brain area which connects to inhibitory cells. FIG. 8B shows a microscale architecture consisting of self-excitation and lateral inhibition (e.g., representative of sensory cortex). Black connections are excitatory and red connection are inhibitory. FIGS. 8C and 8D show a conceptual 2D representation of the vector field without additional input (8C) and with tES-induced macroscale disinhibition (8D) leading to reduced activation of inhibitory (blue) cells. FIGS. 8E and 8F show reachable sets from 3 initial conditions due to sensory input: $v_1 \ldots v_4$ in FIG. 8B. K-horizon reachable sets are shown without tES (FIG. 8E) and with tES induced disinhibition (FIG. 8F). Decreasing the inhibition between excitatory (green) cells results in larger reachable sets, hence visual inputs more easily switch activity between attractors.

However, design strategies in this space of problem are usually predicated on the use of feedback. As previously mentioned, instantaneous feedback is not possible for tES as stimulation artifact greatly limits the ability to collect simultaneous measurements, although technological developments may eventually alleviate this problem by enabling sufficiently fast switching between stimulation and recording states (approximating simultaneous stimulation and measurement). Since the present technology is limited to, at most, intermittent measurements during the stimulation period, another pathway is to model the controller as a deterministic, autonomous dynamical system and analyze reachability (with respect to endogenous control) in the augmented brain-tES space (combining state-variables). This formulation is compatible with open-loop control, or using intermittent measurements for 'resetting' the initial conditions for the tES controller's state-space. In either case, these discussions make clear that there is substantial room for control-theory to co-evolve with neurostimulation, as optimizing non-standard control objectives (reachability properties) may require new forays in basic control theory.

5.5. Evaluating Potential Control Strategies in Large-Scale Models

The combination of the control-theoretic premises outlined above, with aforementioned large-scale brain models, provides an intriguing platform for theoretical and computational research. For example, our recent work has explored how exogenous inputs can be used to shape network vector fields, which can in turn impact the input-output properties. The numerical advances in enabling grey-box models such as MINDy will provide an in silico test-bed for exploring and evaluating the efficacy of control designs, as a precursor to implementation in actual experiments. Reciprocally, these experiments will provide more data to refine models, which in turn will validate hypotheses regarding the dynamical substrates of cognitive function and iterate the development of relevant control objectives.

6. Multiscale Implications of Macroscale Control

In previous sections we have emphasized stimulation for cognitive enhancement which, by definition, involves improving the ability of the brain to solve tasks as opposed to only transmitting information into the brain. However, brain stimulation also finds use in neuroprosthetics and brain-machine interfaces. These applications will especially benefit from the development of controllers capable of manipulating neural microcircuitry due to the information-rich content being transmitted (e.g., for sensory prosthesis to generate percepts). The application of formal control methods to such problems will require consideration of how information is stored/communicated within the target brain areas.

6.1. Brain Neurophysiological Considerations

The degree and manner of neuronal organization varies dramatically between brain areas and this may also have significant implications for control design. Neurons in the human auditory cortex are anatomically organized according to their maximally-sensitive auditory frequency (tonotopy) whereas neurons in early visual cortex are anatomically organized according to positions in visual space (retinotopy) and those in another set of other brain areas are organized according to body parts (somatotopy). Analogous anatomical organizations exist for certain motor responses (e.g., eye movements/saccades), positions in space etc. These organizations arise due to both pre-programmed neural and biochemical factors (concentration gradients) and environmental structure (spatial autocovariance). By contrast, neuronal sensitivity to more abstract concepts, such as different object-categories, do not exhibit analogous spatial structure.

We also note that neuronal organization can occur in multiple ways. In visual areas, the sensitivity of neurons is largely driven by the specificity of brain wiring such that regions sensitive to line orientations within a region of visual-space primarily receive input from lower brain areas which represent light intensity at different 'pixels' within that region of visual space. By contrast, evidence indicates that neurons also separate information based upon the temporal-content of incoming signals potentially due to heterogeneity in their integration time-constants. This feature has been described as a 'Laplace transform' of input to those cells, which has been hypothesized to underlie the representation of temporal contingencies. This operation maps the time-domain of input to the (complex) frequency-domain for storage with cells sensitive to different frequencies.

6.2. Heterogeneity of Neural Dynamics

Regional heterogeneity and structure are thus important considerations for brain-control synthesis. The control of under-actuated systems (e.g., the brain) is intimately tied to the ability to exploit asymmetries in dynamics, states, and/or input strength. Noninvasive methods for measuring brain activity are spatially coarse which presents limited ability to differentiate the activity of different cell-groups. Fine-grained brain control will thus depend upon the ability to leverage neuronal heterogeneity and/or differential stimulation of cell-groups. Neuronal heterogeneity in temporal-sensitivity offers a pathway to neurocontrol using current technology. In this case, it may be possible to selectively recruit cell groups without spatially-precise stimulation. By contrast, groups of homogeneous cells will require differential input for control, which is most easily exploited for brain regions with spatial organization.

One further possibility may be the coupling of anatomically-coarse brain stimulation with sensory inputs. For instance, the brain's representation of semantic categories, e.g. 'mammal', are thought to involve distributed patterns of neuronal activity as opposed to a single, concentrated group of cells. It is likely to be impractical to attempt activating the 'mammal' concept purely using transcranial stimulation alone. The task is trivial, however, using sensory input ('display the word 'mammal"). Neurocontrol methods may therefore benefit from a hybrid approach, in which electrical stimulation is paired with sensory inputs. Primitive variations of this approach have long been used in attempting to shape brain plasticity to improve learning and are now being explored for clinical desensitization in treating phobias and PTSD. Recent studies have demonstrated that acoustic stimuli can be used to entrain brain oscillations to desired frequencies with associated improvements in task performance. Approaches which leverage the neuronal specificity of sensory stimulation with the temporal resolution of tES may thus be especially fruitful.

7. Conclusion

Emerging neural technology and advances in numerical optimization are presenting opportunities for neural engineering. High-resolution brain models (100s of neural populations) are now being identified from noninvasive functional brain data (e.g., EEG, MEG, fMRI), enabling the precise study of personalized brain dynamics. This new generation of brain modeling provides fertile ground in which control theoretic methods will provide a foundation for brain stimulation design and delivery. This intersection also provides opportunity to rethink the objectives of brain stimulation in terms of the underlying latent dynamics, as opposed to operating only within the space of measurements. We have suggested several ways in which control-theoretic methods may be used in the framing of neurostimulation objectives and in particular, to optimize reachability properties of the brain's endogenous control properties, which reflect how environmental information impacts brain activity. This perspective, coupled with the brain's complexity, provides new challenges for formal and numerical control theory. This scenario offers opportunities for mutual growth and therapeutic success in treating neurological and psychiatric disorders.

Example 2

A Real-Time Transcranial Current Stimulation Platform

Transcranial current stimulation (tCS) is a an ex¬perimental brain stimulation treatment that appears to show potential in both treating impairments and improving functional memory. Due to its recent advent and lack of FDA approval, most commercially available tCS platforms are relatively simple and lack real-time capabilities, making experimentation involving closed-loop control systems impossible. This work seeks to remedy this issue by creating a "real-time transcranial current stimulation platform" (RTtCS) that seeks to allow real-time signal generation and improve upon the capabilities of contemporary platforms. The device constructed is able to operate in four modes: as an arbitrary waveform generator, a reference current tracker, a pulse generator and a square wave generator. Each mode was thoroughly tested across both a resistor modelling the impedance of a human head and across the rectus femoris and vastus lateralis muscles of the leg with success observed in both contexts. Promising preliminary results were also gathered in the viability of a closed-loop control system using an EEG in conjunction with the stimulator.

I. Introduction

Transcranial current stimulation or "tCS" is an experimental non-invasive brain stimulation treatment that uses electrical current to stimulate specific parts of the brain. From studies showing promise to "accelerate learning and boost task performance" to being "successfully applied to reduce symptoms of depression", tCS appears to be an technique with a variety of potential applications. Two main methods of tCS have been used for experimentation thus far: transcranial direct current stimulation (tDCS), a method applying a constant current to the scalp, and transcranial alternating current stimulation (tACS), a method applying a consistent sinusoidal waveform to the scalp.

Though offering some flexibility in the experiments that are able to be performed, the methods lack versatility as they both involve pre-generated, constant waveforms. As such, the potential of tCS has been largely unexplored due to the current experimental paradigms. A particularly large unrealized potential of tCS is its role as an actuator in a neural feedback system, that is, using some method of neuroelectrical signal acquisition (for instance EEG recordings) to provide a reference signal to the stimulator in a typical feedback loop configuration. This feedback loop could then be used to realize a closed-loop neuroelectrical control system with potential to improve results found in current literature and grant a better understanding of the effects of tCS as a whole.

Unfortunately, as the treatment is not currently FDA approved, the market of available devices is limited and many, if not all, stimulators are not particularly robust. While some stimulators do offer time-varying signal generation, they only offer offline pre-programming that must take place before the session and cannot respond to external stimulus (such as a reference signal from an EEG). A natural result of this limitation then, is the inability to create this proposed feedback-based control loop.

The present disclosure describes a novel stimulator with real-time signal generation capabilities to rectify this issue. The proposed stimulator makes an improvement to commercially available stimulators in two regards: (1) the ability to generate arbitrary waveforms to be safely applied across the brain in real-time; and (2) the ability to receive some external reference in order to allow the capability of a closed-loop stimulation platform. The following sections describe the construction of the proposed stimulator and provide some preliminary results regarding its capabilities.

II. System Architecture

Figure 9:
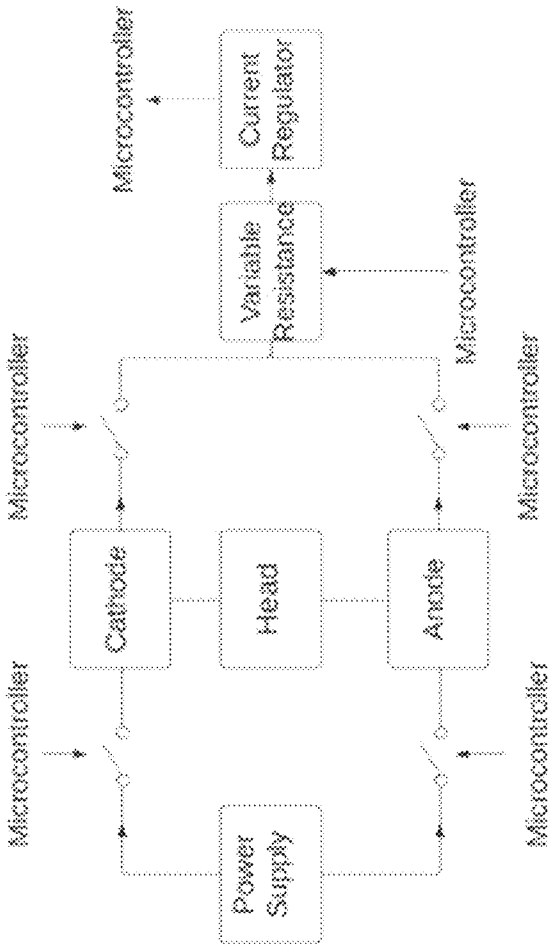
FIG. 9 depicts a high-level architecture schematic of a stimulator.

Using the "transcranial burst electrostimulation device" as a reference for software controlled tCS, the architecture of the stimulator was created. The architecture is described by the high-level block diagram seen in FIG. 9.

The positive terminal of the power supply is connected to the anode and cathode in an H-bridge configuration of switches that are controlled by a microcontroller. This configuration allows for both anodal and cathodal stimulation, meaning that the current can flow either from cathode to anode or anode to cathode depending on the command sent from the microcontroller. This current passes through the user's head in typical tCS fashion and is sent into a variable resistance that is set by the microcontroller. This variable resistance can increase and decrease the current from roughly zero to two milliamps with two-hundred fifty-six intermediate resistance points, allowing for theoretically arbitrary signal generation. The signal then goes into a current regular which creates a hardware maximum current of two milliamps, ensuring the safety of both the user and the hardware itself. Finally, the signal is fed back into the microcontroller so a stable current can be maintained should there be changes in impedance across the head. The microcontroller can be controlled in real-time through a GUI, allowing for straight-forward signal generation.

B. Hardware Description of the Stimulator

Figure 10:
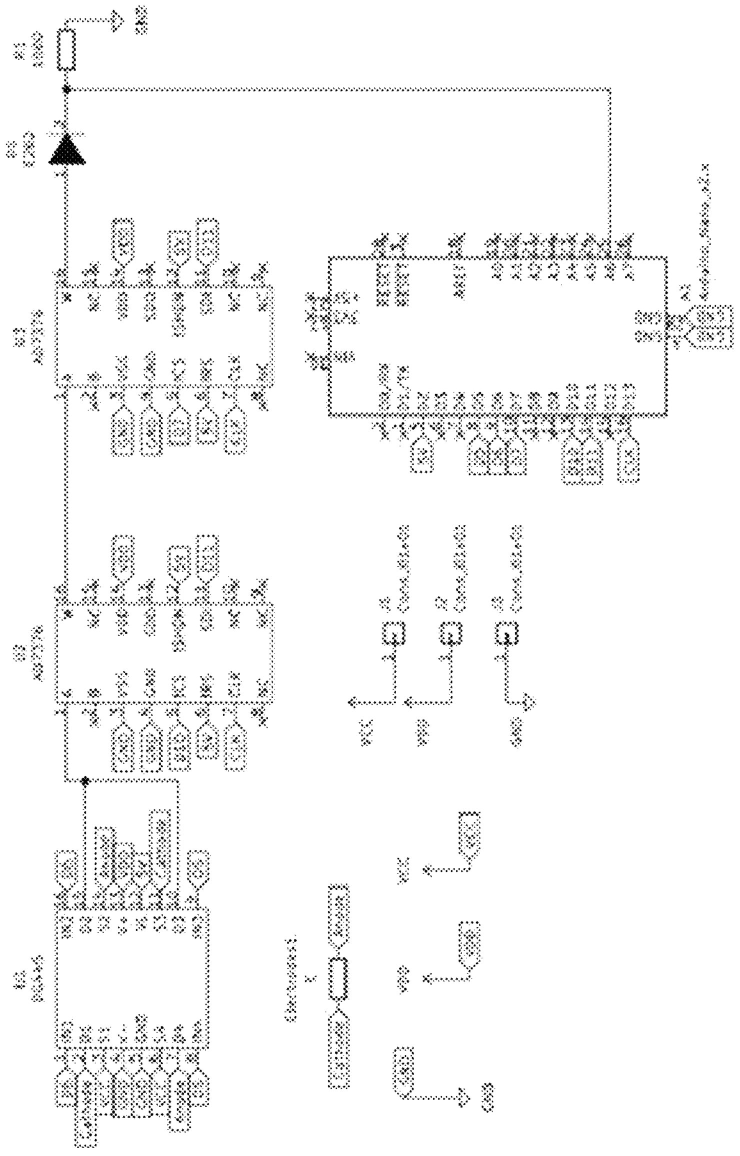
FIG. 10 shows the full circuit diagram of the stimulator.
Figure 11:
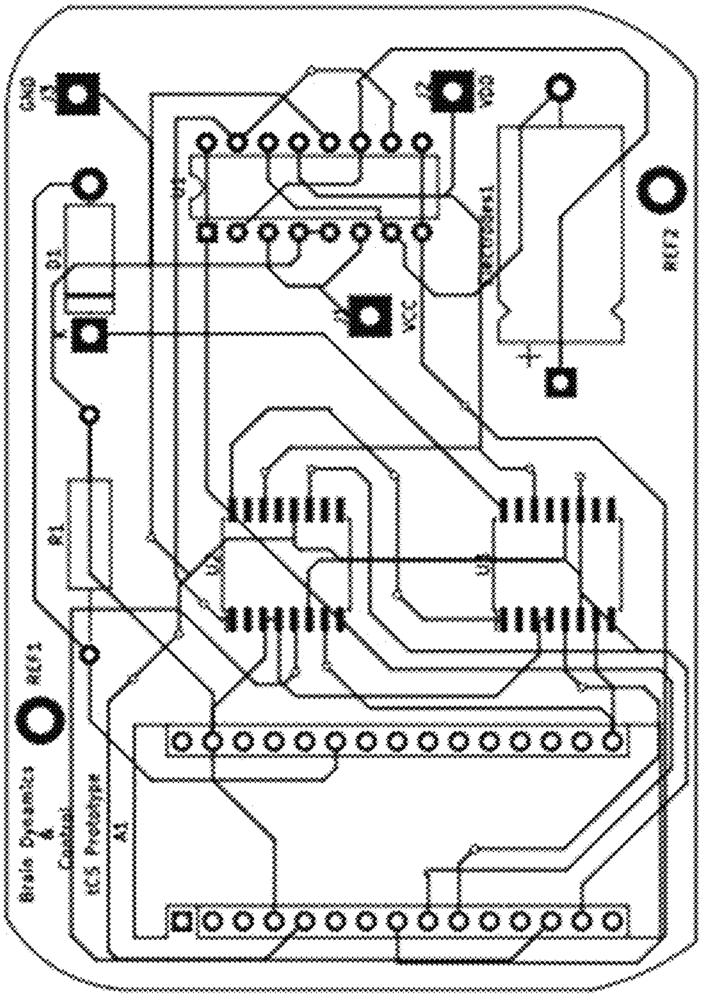
FIG. 11 shows the PCB layout of the stimulator.

FIG. 10 shows the full circuit diagram of the stimulator. Though initially prototyped on a breadboard, a PCB was generated using the software KiCad and sent in for fabrication. FIG. 11 shows the PCB layout that was created.

1) Arbitrary Waveform Generator: When run as an arbitrary waveform generator, the stimulator will prompt the user to provide a text file containing a time-series describing a desired waveform as well as a desired sampling rate. The stimulator will then attempt to repeat this desired waveform until instructed otherwise. For the time being, the time-series must be constructed by hand and written into the driver file before it can be used.
2) Reference Current Tracker: When run as a reference current tracker, the stimulator will attempt to match the current provided as reference either though direct user input or through an external input to the microcontroller. This mode of operation best lends itself to feedback operation and is able to quickly respond to quickly changing reference values.
3) Pulse Generator: When run as a pulse generator, the stimulator will prompt the user to provide the number of pulses desired, the amplitude of the pulses, the DC offset of the pulses and the duty cycles (on/off time) of the pulses. The pulse will then be repeated until the user chooses to end the session.
4) Square Wave Generator: When run as a square wave generator, the stimulator will prompt the user to provide a low resistance value, a high resistance value and a desired frequency. The square wave will then be generated until the user decides to end the session.

III. Results & Analysis

A. Physical Implementation

Figure 12:
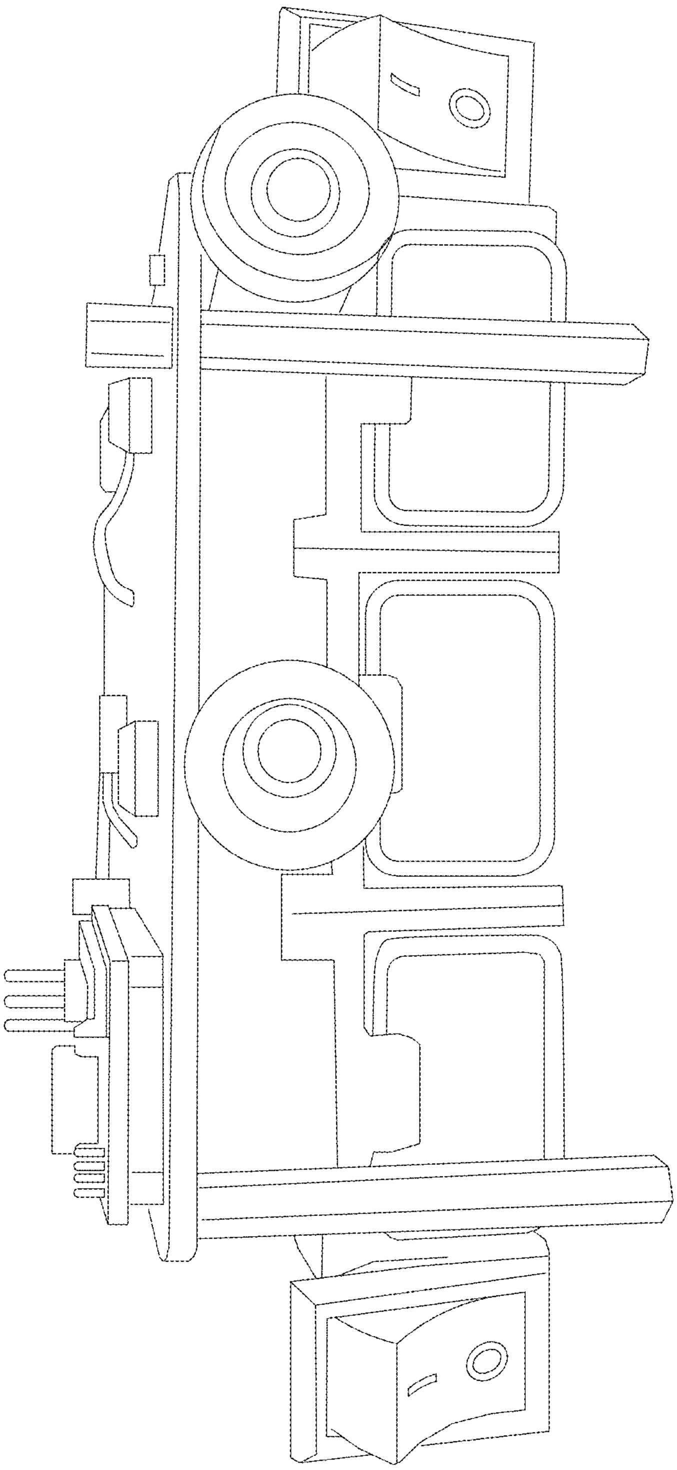
FIGS. 12 and 13 show the front profile and overhead view of the stimulator.
Figure 13:
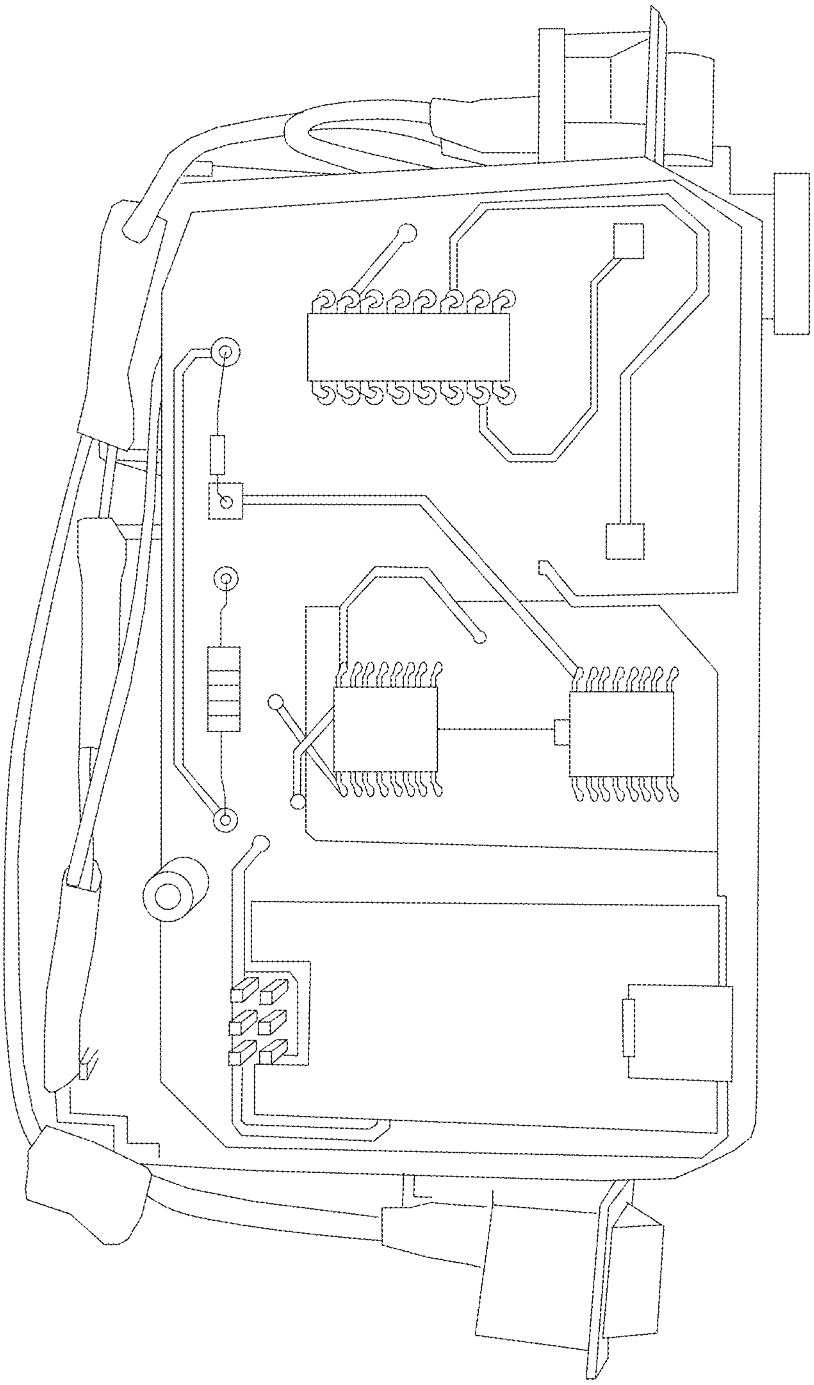

FIGS. 12 and 13 show the front profile and overhead view of the stimulator created.

The right-hand switch allows the digital potentiometers and switching IC to receive power while the left-hand switch allows the voltage to be applied to the anode and cathode, serving as a physical kill switch to end a session. The right hand banana-plug jack is where the anode is to be plugged in and the left-hand banana-plug jack is where the cathode is to be plugged in. The correct order of powering the stimulator is important as applying a voltage across the ICs without powering them can cause undefined behavior. As such, the correct booting procedures involves: (1) turning the right-hand switch on; (2) plugging the Arduino Nano into your computer with its micro-USB port; and (3) turning the left-hand switch on when you are ready to begin the session. Powering off the stimulator follows the same steps in reverse order.

B. Arbitrary Waveform Generator

Figure 14:
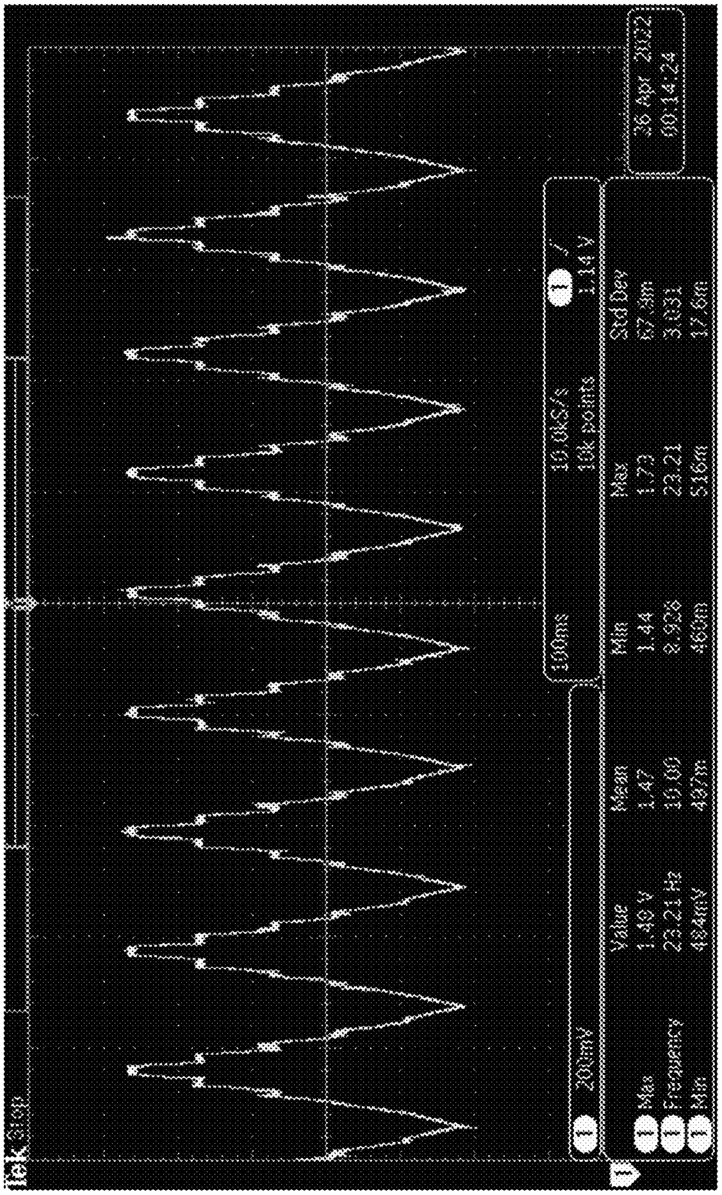
FIG. 14 shows a triangular wave produced by the stimulator.
Figure 15:
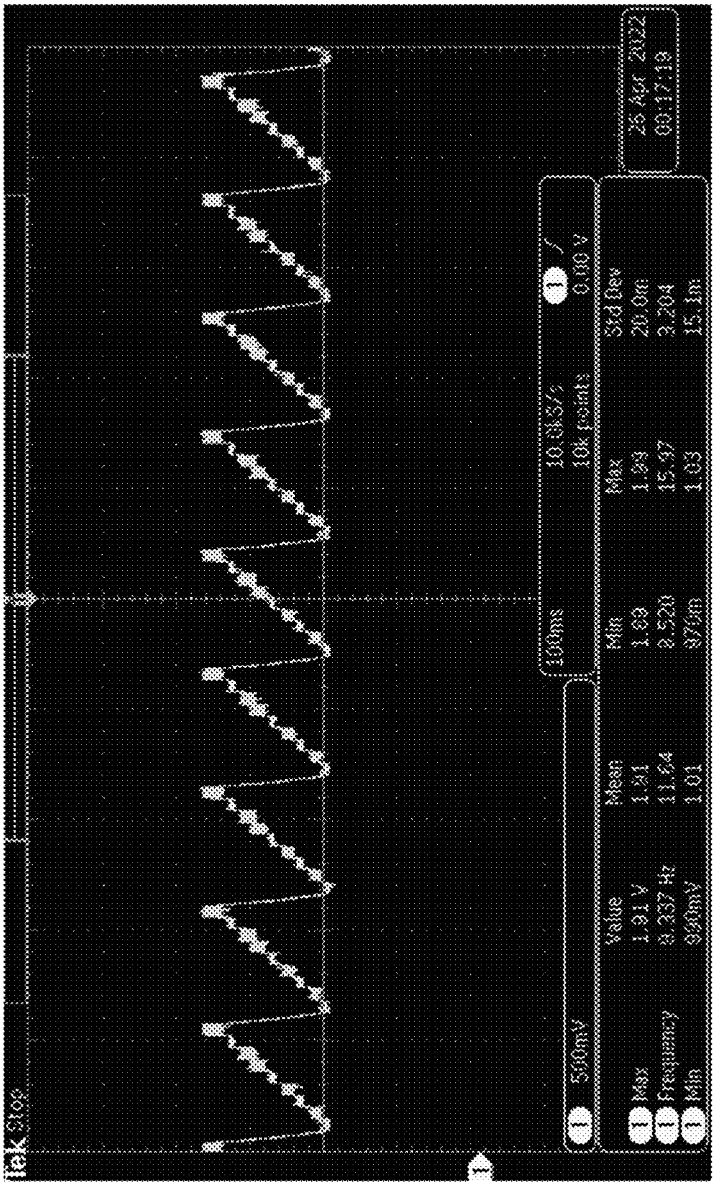
FIG. 15 shows a saw-tooth wave produced by the stimulator.

The stimulator is able to successfully generate arbitrary waveforms based on a given time series. FIGS. 14 and 15 show two possible waveforms produced by the stimulator across a resistor modelling the impedance of the head. FIG. 14 shows a triangular wave and FIG. 15 shows a saw-tooth wave.

A key performance note is that the current implementation of the arbitrary waveform generator allows a mini-mum sampling time of 10 milliseconds, that is, a time series with steps smaller than 10 milliseconds cannot be used. The current software implementation is not fast enough to keep up with sampling rates higher than this and are therefore disallowed from use at all. It is postulated that this is strictly a software limitation and a more efficient implementation of the function will likely allow shorter sampling rates.

C. Reference Current Tracking

The stimulator's reference current tracking is able to match the reference to within 0.1 milliamps for reference currents greater than 1.5 milliamps and to within 0.05 milliamps for reference currents smaller than 1.5 milliamps. The tracker was originally designed to attempt to match the reference exactly, however a range was given in order to avoid thrashing between a current above the reference and below the reference continuously in the case that the exact reference cannot be reached due to the discrete nature of the potentiometers. Additionally, the software only allows the wiper of a single potentiometer to change by one every fifty milliseconds in order to reduce discomfort in the user. This limitation was enacted in order to mirror the purpose of a ramp-up and ramp-down period commonly found in many tCS procedures.

D. Pulse Generator

Figure 16:
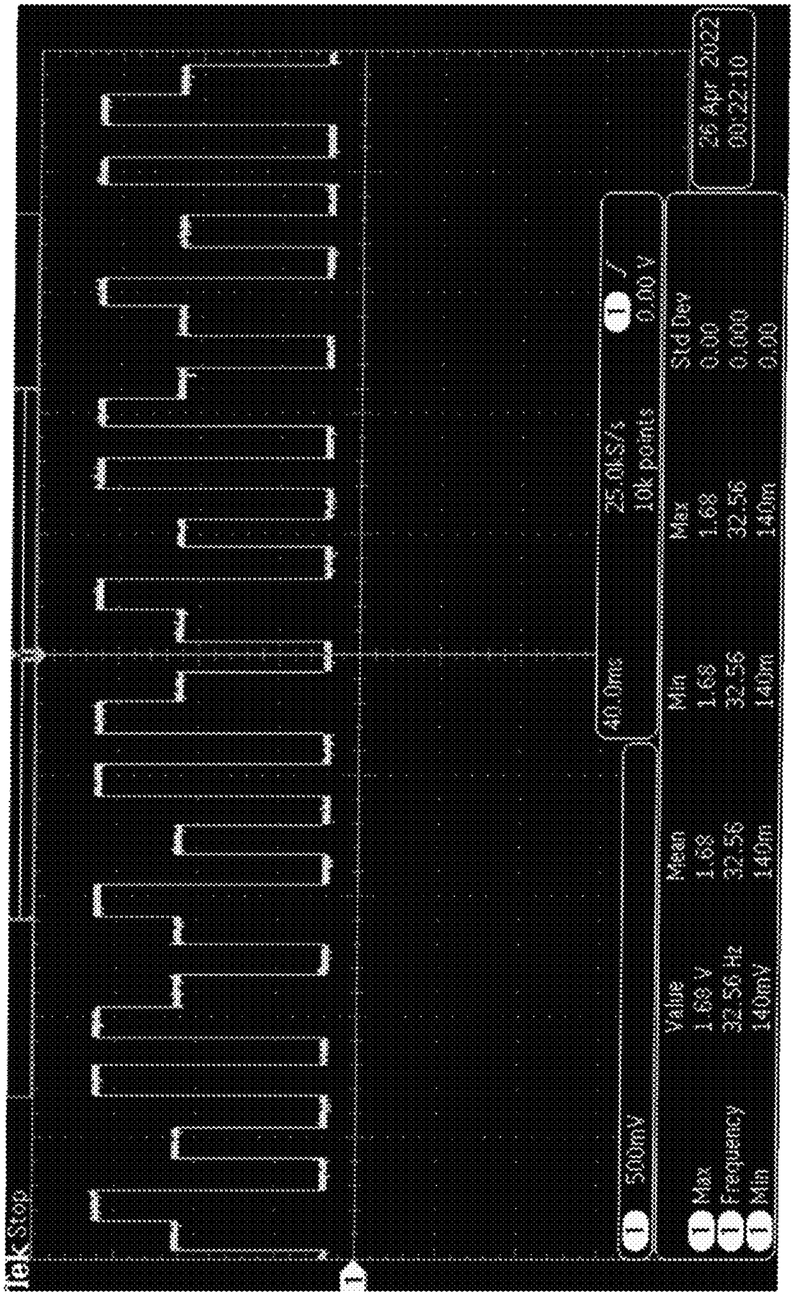
FIG. 16 shows an example pulse train produced by the stimulator across a resistor modelling the impedance of a head.

The pulse generator mode of operation was designed to be able to take up to one-hundred pulse inputs from the user with a minimum time between pulses of one millisecond. This one millisecond time restriction was decided arbitrarily and faster performance can likely be found should that be desirable in the future. While this mode is quite versatile, its efficacy in tCS procedures is questionable and it is more intended to be a debugging tool when recording EEG measurements in order to determine which signals are from the stimulator and which are from brain activity. FIG. 16 shows an example pulse train produced by the stimulator across a resistor modelling the impedance of a head.

E. Square Wave Generator

Figure 17:
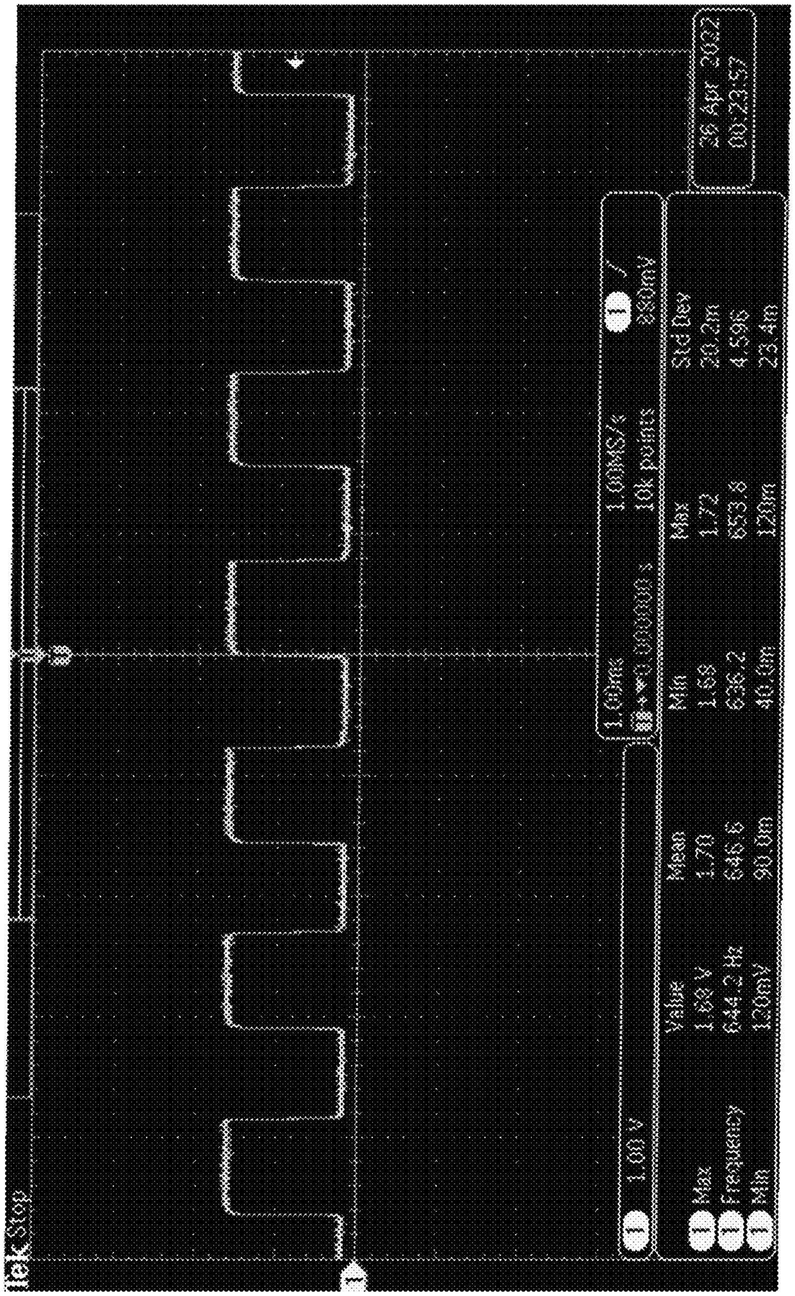
FIG. 17 shows the square wave produced across a resistor modelling the impedance of a head at 650 Hertz.

The square wave generator mode of operation is able to produce consistent square waves between 1 Hertz and 650 Hertz from −2 to 2 milliamps or anywhere in between. The limitation on the high end is due more to the speed limitations of the Arduino Nano than the hardware limitations of any of the IC parts. It is not likely that frequencies higher than this are desirable and as such software improvements have not been investigated. Similarly to the pulse generator function, it is not clear if square waves are desirable in tCS procedures, though they are very useful in EEG measurement debugging. FIG. 17 shows the square wave produced across a resistor modelling the impedance of a head at 650 Hertz.

F. Preliminary Results Across Skin

Figure 18:
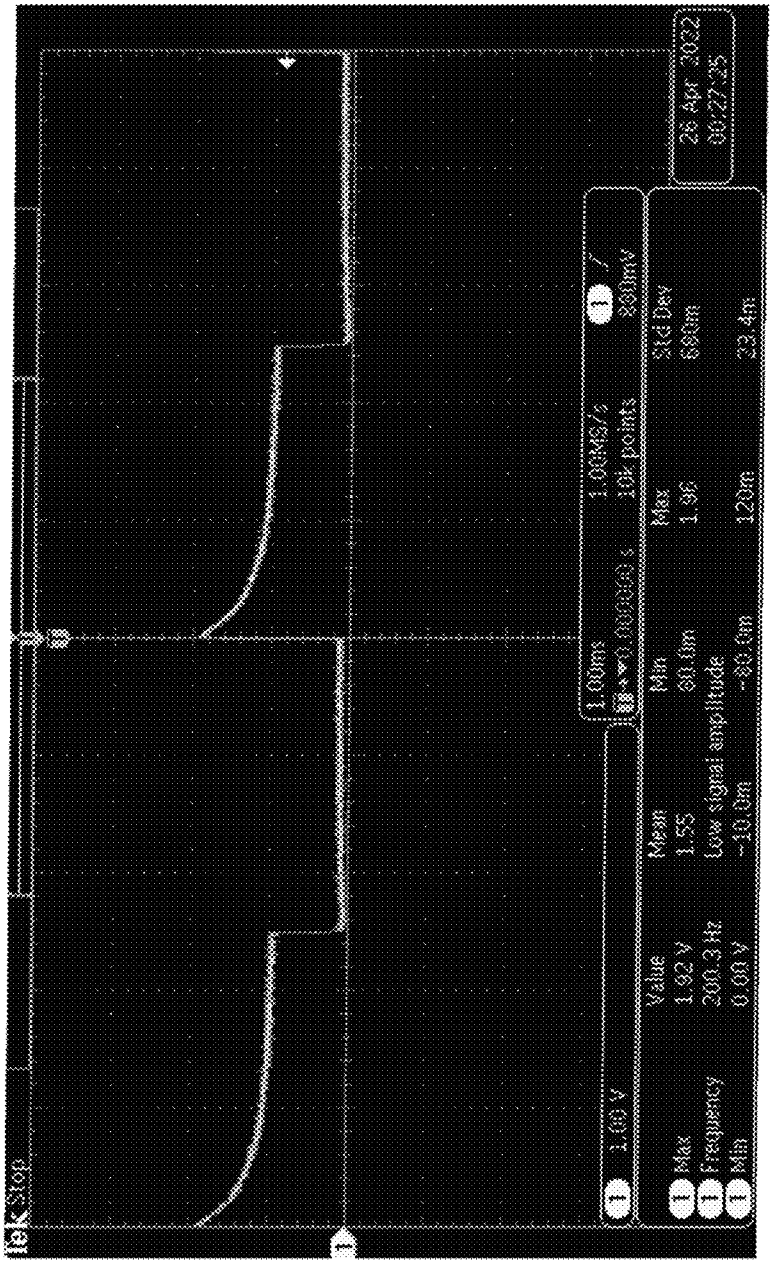
FIG. 18 shows the low-passing effect of the skin for a 200 Hz square wave.

As the device is currently being reviewed by the institutional review board, a significant amount of data was not able to be gathered with the anode and cathode across a head. However, data was generated with the anode and cathode across the rectus femoris and vastus lateralis muscles of the leg. These experiments resulted in two interesting results: an observed decrease in skin impedance over time and a low-passing effect created by the skin's parasitic capacitance. It was observed that the current across the leg would slowly increase over time with no changes to the wiper values of the potentiometers. It is postulated that the skin's impedance decreases as current is continuously applied, implying that the closed loop system created for the stimulator is indeed a necessary factor if a constant current is desired. FIG. 18 shows the low-passing effect of the skin for a 200 Hz square wave. While this effect is quite obvious in this case, it is unclear whether or not this is an issue in the context of further experimentation.

G. Preliminary Results with EEG

Figure 19:
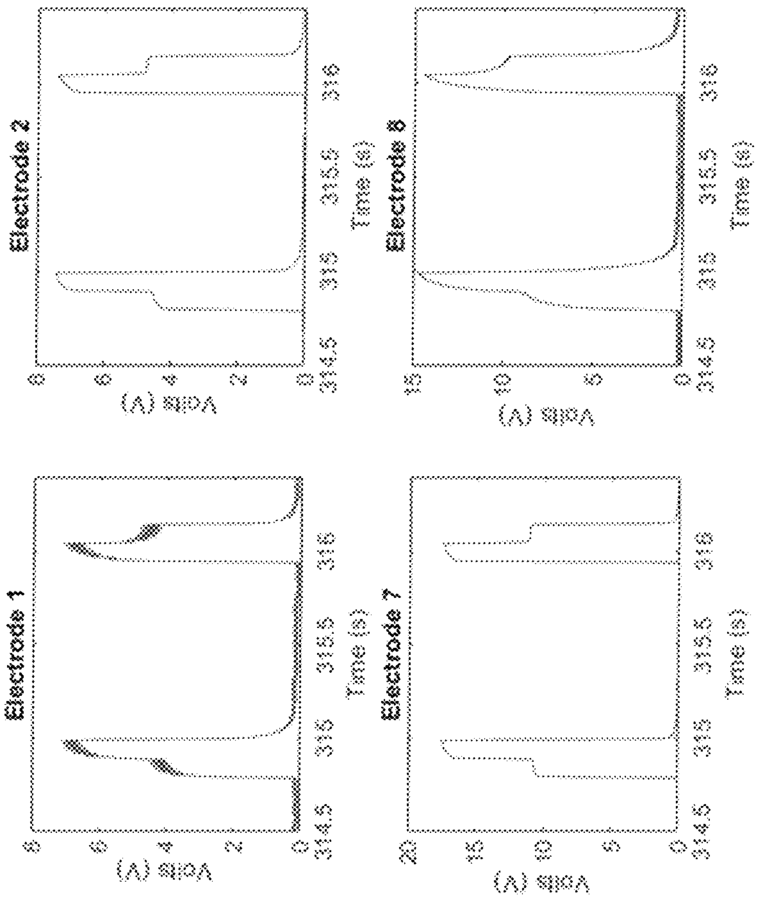
FIG. 19 depicts initial results that show rise and fall times of arbitrary pulses.

The data that was able to gathered across a human head was done so with an electroencephalography (EEG) setup. In order to work towards the desired closed loop feedback system involving EEG, the controller must be able to delineate between the electrical signals created by the brain and those created by the stimulator. The initial results gathered (seen in FIG. 19) show that the rise and fall times of arbitrary pulses applied across the head are short enough such that any brain activity in response is likely going to be able to be effectively measured without residual noise from the stimulator.

IV. Conclusion

Despite some limitations, the stimulator is successfully able to serve as a real-time platform for transcranial current stimulation as well as offline arbitrary function generation. Though the stimulator is now able to be used as an actuator for a neural control system, the system itself now must be designed. The clear next step towards the goal of a closed-loop system is further experimentation with the stimulator run in conjunction with an EEG in order to determine the nature of the controller and the ability to gather clean EEG data while the stimulator is providing current. Overall, the preliminary results generated appear quite promising.

Appendix A

Safety Analysis

Of the numerous published studies using tDCS, there have been no significant adverse events recorded when stimulation is applied according to standard safety guidelines. The device itself follows a standard tDCS design in series with a digital potentiometer to down-regulate and modulate the typically used 2 mA maximum current. The FDA has deemed previous tDCS trials as NSR. Meta-analyses have not found a statistically significant increase in reports of any adverse event due to using a tES device relative sham conditions (wearing an inactive device).

Appendix B

List of Materials

Table I provides a list of materials used by the stimulators, a description of each part and their manufacturer.

TABLE I

List of Materials Used

| Part Name | Quantity | Description | Manufacturer |
|---|---|---|---|
| AD7376 | 2 | 100 kΩ Digital Potentiometer | Analog Devices |
| Arduino Nano | 1 | Microcontroller | Arduino |
| DG445 | 1 | Quad Normally Open Switch | Maxim |
| E202 | 1 | 2 mA Current Limiting Diode | Semitec |
| 1 kΩ Resistor | 1 | 5% Resistor | BOJACK |
| 9 Volt Battery | 3 | Power Supply | Duracell |

Example 3

System for Personalized Inference of Transcranial Current Stimulation Waveforms

Background

Transcranial electrical current stimulation (tCS) is a non-invasive technology for manipulating brain electrical activity. tCS has been shown to modify or enhance cognitive functions, including working memory, making it an attractive candidate for development in rehabilitation contexts. However, a major challenge of contemporary tCS paradigms has been the reliance upon predetermined, open-loop protocols which prohibit robust engineering designs based upon adaptation or feedback.

In the current work, we developed a novel tCS device capable of real-time stimulation and control via an embedded microcontroller. We established performance specifications on our device and its interactions with concurrently recorded EEG. We used impulsive tCS waveforms to test the spatial and temporal extent of artifacts generated by our device on concurrent EEG. We then conducted a pilot experiment to verify the operation of the device in a practical format.

Design & Specifications

Figure 20:
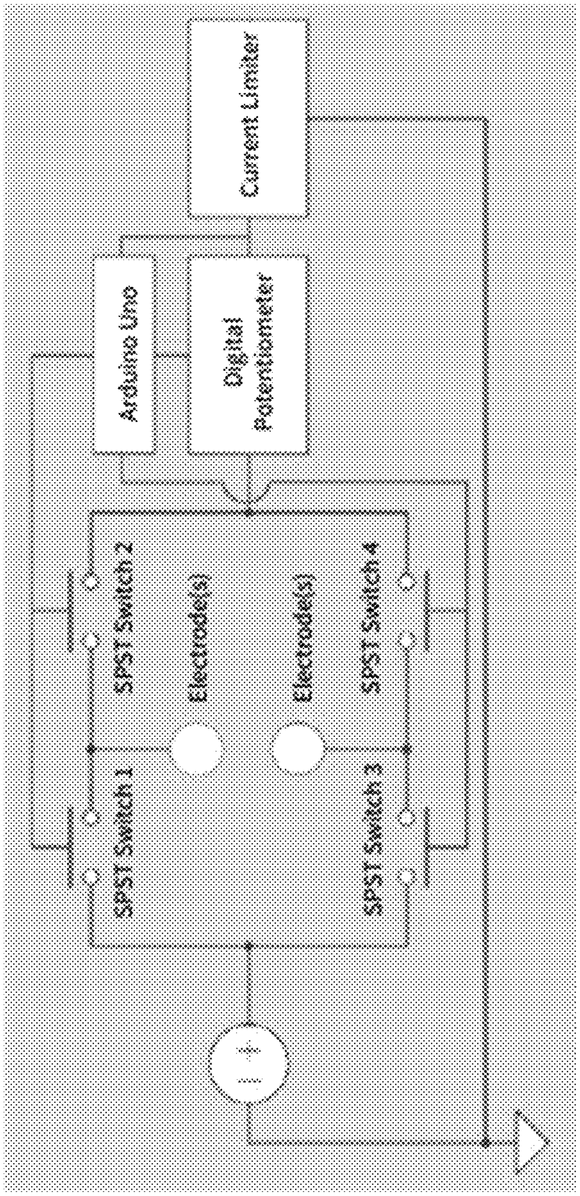
FIG. 20 depicts a schematic of the tCS device.

Referring to FIG. 20, the tCS device utilizes a Quad-SPST switch design in conjunction with a digital potentiometer to modulate the amplitude and polarity of the delivered waveform in real time. A hardware-based current limiter ensures a safe level of current delivery and allows for real-time impedance tracking.

Figure 21:
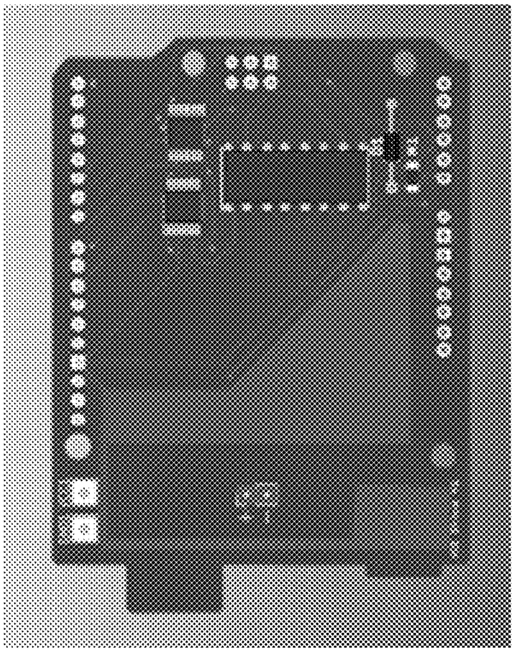
FIG. 21 depicts the PCB layout.

Device Results (See FIG. 21)

115200 Baud (Maximum) allows for real time host to tCS device communication. Arduino Uno shield design increases ease of use and allows for full programmability. 1 millisecond resolution for arbitrary waveform shaping.

Stimulation Artifacts

Figure 22A:
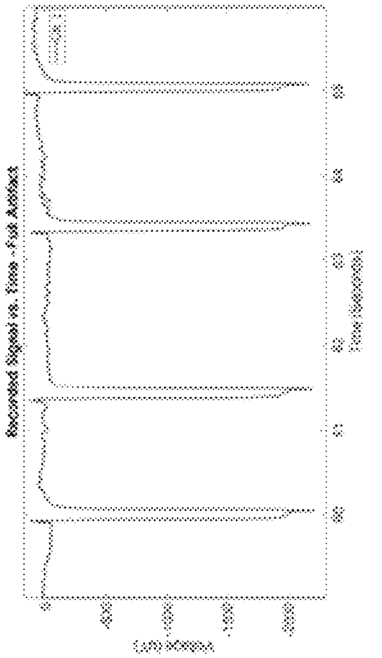
FIGS. 22A and 22B depict the stimulation artifacts.
Figure 22B:
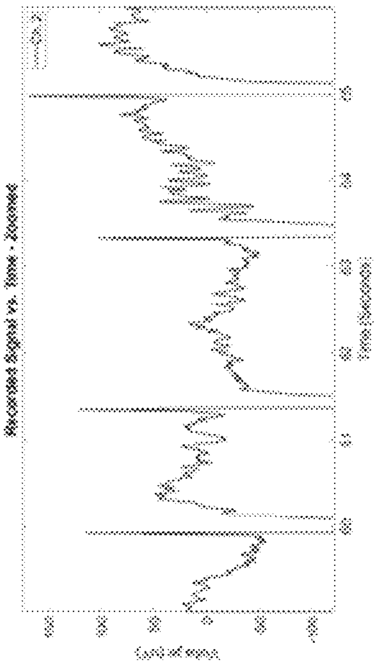

Refer to FIGS. 22A and 22B.

Pilot Experiment

Figure 23A:
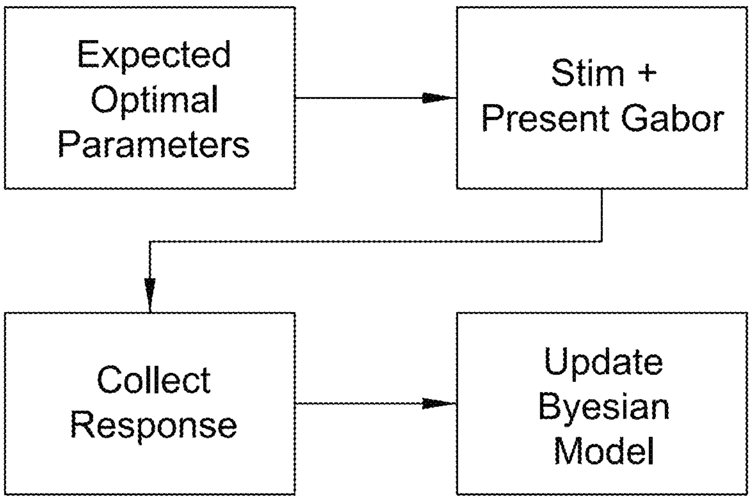
FIG. 23A depicts a method executed by the tCS device.
Figure 23B:
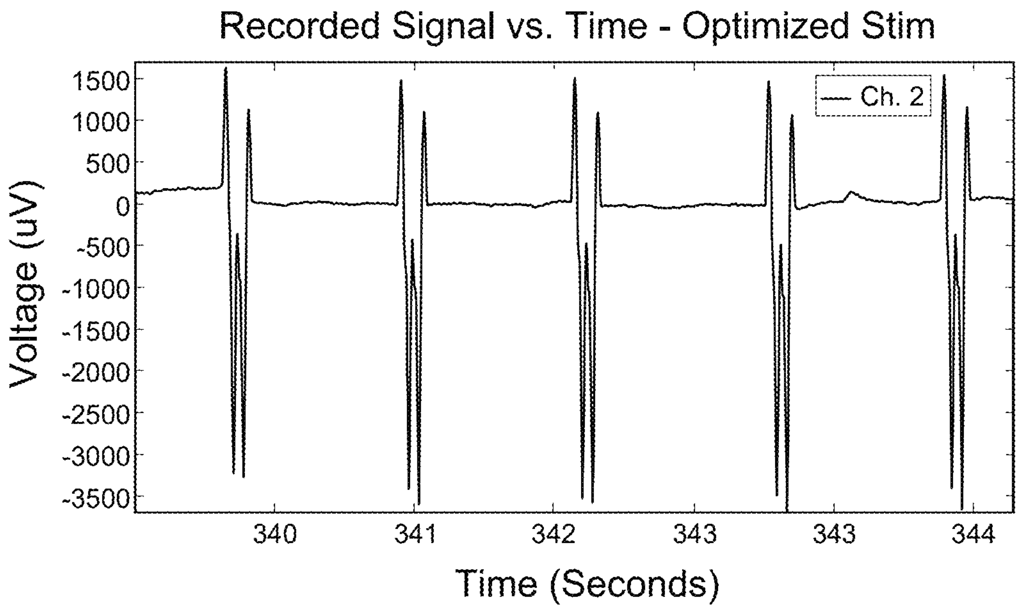
FIG. 23B demonstrates the short-lived stimulation artifact and feasibility of a combined EEG/tCS system.

Referring to FIGS. 23A and 23B, the stimulator was run in conjunction with an EEG cap to demonstrate the short-lived stimulation artifact and feasibility of a combined EEG/tCS system.

A Bayesian optimization was run on two parameters of a ramped sine signal described by I(t)* to attempt to increase task performance relative to a sham signal.

$$*I(t)=\alpha\ \sin(((2.5)2\pi t)+0.5\ \sin((\beta)2\pi t)$$

Experiment Task

Figure 24:
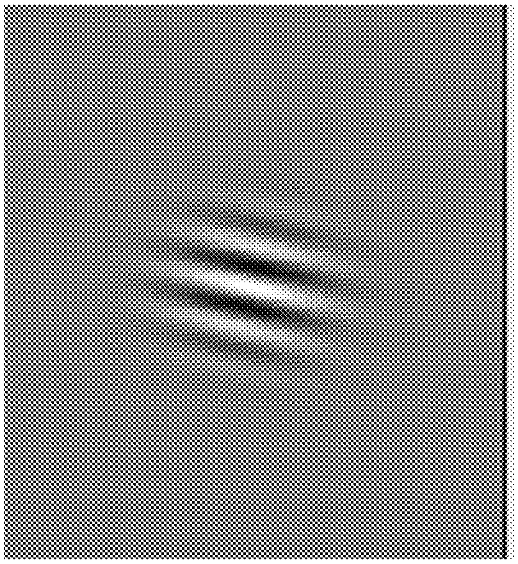
FIG. 24 depicts a rotated Gabor grating.

Rotated Gabor gratings (see FIG. 24) were presented for 650-750 milliseconds to participants who were then asked to identify the direction of rotation as quickly as possible. Electrical stimulation was delivered in blocks before and during grating presentation with each stimulation pattern being interleaved with sham blocks.

Task performance is evaluated by the difference of the average response times for the real and sham waveforms.

Example 4

High-Level Description of System and Method

The closed-loop non-invasive neurostimulation system delivers immediate transcranial electrical stimulation of the brain in response to either direct user-control or programmatic instructions determined by measurement of physiological activity. The system contains a dedicated stimulation device and digital computers that send instructions to the device, specifying the time-course of electrical current delivery. The stimulation device operates in real-time and continuously adjusts current as new instructions are received from the computer. The device uses internal measurements to continuously adjust voltages applied to the scalp to compensate for individual differences in anatomy. The computers simultaneously monitor behavior and/or brain activity in the stimulation subject and estimate mathematical models of how neurostimulation impacts behavior and/or brain activity in an individualized manner. The computers programmatically control the neurostimulation device so as to maximize model predictions of a de-sired outcome.

List of Potential Applications

The system and method for non-invasive brain modulation has potential applications in both monitoring and modulating properties of the nervous system.

Diagnostic applications to localizing sources of brain disease based upon electrophysiological response to neurostimulation, as informed by brain dynamical models.

Diagnostic applications to monitoring changes in brain health based upon electrophysiological response to neurostimulation.

Diagnostic application to monitoring and predicting brain activity based upon electrophysiological response to neurostimulation.

Improving cognitive functions, including memory and attention, in healthy and patient populations.

Suppressing pathological brain activity, including seizures, by responsive neurostimulation.

Decreasing anxiety and depression by interacting with associated brain activity.

Example 5

Figure 25A:
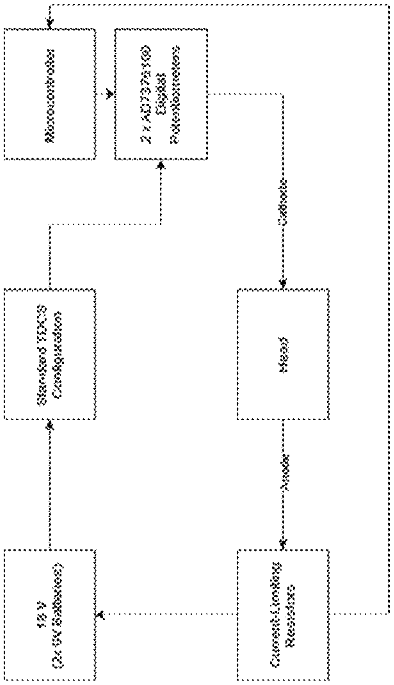
FIGS. 25A and 25B depict a custom tDCS design.
Figure 25B:
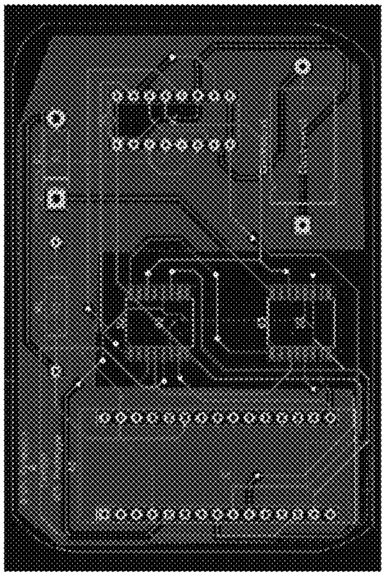

With reference to FIGS. 25A and 25B, a custom tDCS design is shown. Custom Hardware: Dr. Ching's lab also has also designed and built a low-latency custom tES system designed for closed-loop and real-time stimulation environments. The device includes a constant power supply in the form of two nine-volt batteries that is fed into a standard tES circuit configuration. This configuration by itself would provide a constant two milliamps of current across the wearer's head. Attached in series with this circuit are two AD7376100 digital potentiometers. These potentiometers serve to variably decrease the current supplied by the previous circuit elements. The two potentiometers are controlled by a micro-controller (an Arduino Nano) that is able to detect and adjust the current flowing through the circuit. The output of the digital potentiometers is then fed into a standard 2-inch×2-inch electrode used as the tES cathode. An identical electrode would be placed which would serve as the anode of the device. This anode would then feed into a set of resistors AND current-limiting diode, used to limit the current to a maximum of 2 mA. The voltage across these resistors serves as source of the microcontroller's knowledge of the current within the circuit. The output of the current-limiting resistors is then connected to the negative terminal of the power supply, completing the circuit (see FIG. 25). Overall, this custom design allows for near real-time modulation of stimulation current and delivery of fully specifiable tES waveforms with low latency.

Example 6

Causal manipulation of physiology is a bedrock of scientific research and therapeutics, and a key component of systems neuroscience research with non-human animals. In contrast, in cognitive neuroscience studies, the ability to test mechanistic hypotheses regarding the relationship between brain and cognitive function in humans has been impeded by the limitations of current noninvasive technologies available for use with non-clinical research participants. Advancing methods and technology for noninvasive brain stimulation have aimed to fill this gap. One of the most promising approaches in this regard involves transcranial electrical stimulation (tES), which can allow for many independent stimulation channels. Such technology facilitates the manipulation of distributed neural processes (e.g., brain networks), which may be critical for treating certain psychiatric disorders. Yet the ability to interpret the results of tES experiments (particularly null findings), depends upon the efficacy/reliability of stimulation in modulating neural activity. Inferences also rely upon the ability to identify neural consequences (e.g., downstream effects) of tES. Consequently, new approaches, which broaden the scope of tES, or improve its efficacy, strongly advance both mechanistic theory and clinical translation within human neuroscience research.

Individual-Specific Stimulation Protocols. Historically, tES paradigms have been largely influence by 'dose-response' study designs, in which a pre-set current waveform is repeatedly delivered to each subject. However, the inconsistent outcomes observed across participants suggest that neurostimulation research may benefit from a personalized-neuroscience approach, which considers individual differences in brain/head structure, neural circuits, and function. State-of-the-art approaches now use subject-specific electrode-placement to account for anatomical differences. This process has improved the anatomical accuracy of tES targeting. However, a growing consensus has emerged that the variable efficacy of tES is not only due to anatomical variability, but also to individual differences in brain networks and their dynamics. Recent studies have begun to explore these influences, but still without the model-based approach or analytic techniques that are critical for estimation of latent dynamics or optimization of waveform delivery. A promising study for instance, demonstrated that AC neurostimulation (tACS) was only effective when delivered at each subject's peak EEG frequency within the 'theta'-band (measured at rest). Advancements in individualized stimulation protocols, i.e., personalized tES, will play a critical role in enhancing tES efficacy, the ability to perform causal manipulations as a human neuroscience research tool, and most importantly, in improving therapeutic outcomes.

From Stimulation to Control: Engineering Frameworks for tES Design. Current frameworks for tES design are centered upon the common belief that the neural response to stimulation follows the time-course of injected current (i.e., that 8 Hz sinusoidal stimulation will optimally promote 8 Hz power). The successful application of this approach within the current literature indicates that such a premise may be appropriate in some instances. However, even these results are likely suboptimal. As a dynamical system, the brain's response to a current injection is a function of not just the stimulation waveform, but also the brain's intrinsic dynamics and 'initial conditions' (the brain activity state at the stimulation onset). Previous studies have heuristically incorporated such ideas. For instance, a key innovation was tuning tACS to match each subject's peak resting-state frequency, and in delivering tACS in-phase with EEG. Yet, no study to date has employed control-systems methodology as the means by which to directly optimize tES delivery. Indeed, established methods from control-theory provide a rigorous and potentially more powerful framework for optimal tES input-design. However, they require a formal computational model describing the underlying neural architecture and dynamics. If such a model is available, neural control engineering methods provide formal methods for input-design, while also taking into account issues such as model-uncertainty and noise. Neural control engineering approaches can also optimize objectives that are not readily treated otherwise, such as indirectly manipulating latent state-variables (i.e., brain areas, neural populations) that are not directly actuated by the stimulating electrode(s). The integration of neural control engineering approaches with neurostimulation thus has the potential to substantially improve tES efficacy and to dramatically broaden the scope of tES objectives.

Innovation

The proposed research will validate and test a novel and highly innovative framework from which to conduct neurostimulation research. In particular, our project utilizes formal optimization and control techniques to model individual brain dynamics, which in turn yields principled stimulation objectives from which to link these dynamics with testable changes in cognitive functioning.

Individualized Brain Modeling with M/EEG. The present disclosure is grounded in our past success in developing Mesoscale Individualized NeuroDynamic (MINDy) models, derived from single-subject resting-state brain imaging data. The MINDy model, estimated individually for each participant, takes the form of a nonlinear dynamical system containing hundreds of interacting neural populations (brain regions). These models are parameterized in terms of both the directed connectivity between brain regions, and the local characteristics of each brain region (its activation function and decay-rate/time-constant). All parameters are estimated directly from brain activity time series, so that the resulting models can be explicitly simulated to predict future brain activity. In resting-state fMRI, we have demonstrated that the paradigm is reliable and robust to motion, preprocessing choices, and hemodynamic variability. The MINDy models estimated from resting-state fMRI also generalize to task fMRI contexts (i.e., yielding improved estimation of task-evoked activation).

Figure 26A:
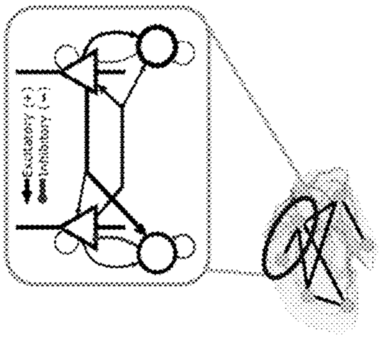
FIG. 26A depicts M/EEG data with two regions including excitatory cells and local inhibitory cells.
Figure 26B:
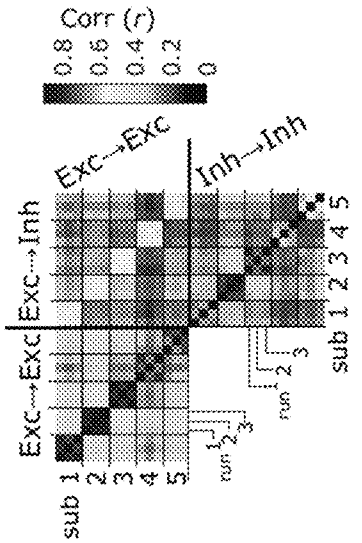
FIG. 26B shows long distance connections.
Figure 26C:
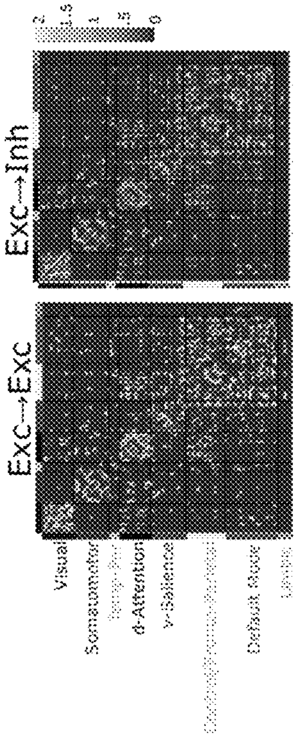
FIG. 26C depicts group average long distance connections.

More recently, we have expanded this technique to model M/EEG data using a novel optimization technique based on the Kalman Filter. Referring to FIG. 26A, each region has two populations: excitatory cells and local inhibitory cells. As shown in FIG. 26B, estimated long distance connections are reliable. FIG. 26C depicts group average long distance connections (E->E and E->I). These models, which we utilize in the current study, leverage the temporal resolution of M/EEG to further estimate interactions between excitatory and inhibitory neural populations at each brain region (100 total). Separate long-distance interactions are estimated for excitatory-to-excitatory and excitatory-to-inhibitory projections. The description of multiple neural populations per region (excitatory and inhibitory) is necessary to describe the mechanisms underlying oscillations and other activity at M/EEG time-scales. Parameters are directly estimated from channel-level measurements using the Kalman Filter to exploit spatiotemporal dependencies in the excitatory (x) and inhibitory (r) populations:

$$x_{t+1}=W_{E\psi}(x_t)-\beta_{E\zeta}(r_t)+D_E x_t+\omega_E(t)$$

$$r_{t+1}=W_{I\psi}(x_t)-\beta_{I\zeta}(r_t)+D_I r_t+\omega_I(t)$$

$$\text{EEG}_t=-Lx_t+\varepsilon_t$$

In this model, the excitatory and inhibitory depolarizations are transformed into activation (i.e., firing-rate) via the parameterized (region-specific) sigmoidal functions ψ and ζ, respectively. The parameters W, β, D denote, respectively, connections from excitatory cells, (local) connections from inhibitory cells, and the activation time constant/decay-rate. Physiological noise is denoted ω. The EEG signal is modeled via the multiplication of dipoles formed by excitatory cells ($x_t$) with the 'lead-field' model (L) of head conductance (computed from MRI) with measurement noise ε. To make this estimation problem robust, we constrain eligible connections in W based upon group-level fMRI MINDy models from a separate dataset. Noise covariances are estimated using established methods. Recent results by our group indicate that M/EEG MINDy models are reliable, individualized (subject-specific), and accurately predict future M/EEG activity.

Figure 27:
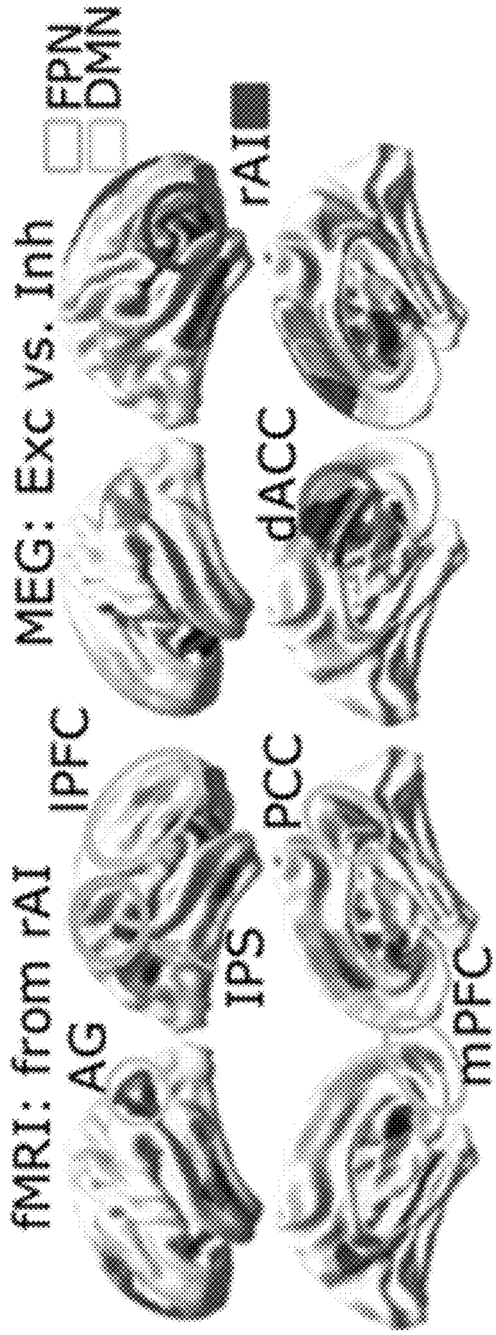
FIG. 27 depicts M/EEG data.

Formalizing Complex Phenomena (Brain Network Switching). Another key innovation of the project is our use of neural control engineering approaches, which provide a framework from which to formalize abstract objectives (i.e., enhancing the ability to switch between brain network states), such that they can be optimized via neurostimulation paradigms, and directly investigated in tES experimental protocols. In particular, we examine hypotheses related to the 'triple-network model', which postulates that the SAL network, with core nodes in the anterior insula (AI) and dorsal anterior cingulate cortex (dACC), is critical for switching the brain from DMNdominant (internally-oriented attention) to FPN-dominant (externally-oriented attention) mode. The triple-network model has been highly influential within clinical neuroscience research, because it provides a unifying account, in which key aspects of cognitive dysfunction in many forms of psychopathology (e.g., schizophrenia, depression, dementia, autism) arise from aberrant dynamics within these networks. Although an obvious neurostimulation based intervention approach might be to attempt to counteract a bias toward one brain network mode (e.g., DMN dominance) by directly inducing network switching, it may actually more effective therapeutically to instead enhance the brain's capacity to switch among networks, when contextually appropriate. Here, we propose to formalize this capacity in terms of "reachability", a well-defined metric derived from control theory. In particular, the 'reachable set' describes all patterns of distributed brain activity that can be obtained by modulating the activity of input nodes. We quantify how many outcomes can be produced (per unit energy of modulation) by the volume of this set. Thus, the reachability of region(s) $\{A_i\}$ modulating region(s) $\{B_j\}$ measures how many reconfigurations of $\{B_j\}$ can be obtained by altering the spatiotemporal activity of {Ai} (per unit-energy=sum of squares). In the (nonlinear) brain, reachability is state-dependent, i.e., a function of the ongoing activity throughout the brain. Reachability thereby provides a model of how the spatial distribution of brain activity shapes the influence ("effective connectivity") of one brain region or network on another. We have conducted preliminary analyses to examine the triple-network account and reachability effects in MINDy models. developed from both fMRI (FIG. 25A) and M/EEG data (FIG. 27). Specifically, the triple-network model indicates that SAL regions should exhibit positive outgoing connections to FPN and negative outgoing connections to DMN. These linkages should also be comparatively stronger than FPN-DMN connections indicating that SAL can promote switches between these networks. Moreover, SAL connections to DMN should be stronger than those received from DMN as their relationship is guided by top-down control. We found that, irrespective of modality (fMRI or MEG), MINDy models were consistent with this network architecture, particularly in terms of right AI (rAI) connectivity, indicating that the MINDy technique is well-suited to study this system (FIG. 27). Moreover, using these MINDy models, we could successfully compute reachability, solving for conditions under which potential inputs to rAI (due to salient stimuli) maximally move neural activity along the FPN vs. DMN axis.

Alignment with programmatic interests. The present disclosure is well-aligned with PAR-21-176, as we will 'test whether modifying electrophysiological patterns during behavior can improve cognitive processing.' We are especially responsive to Topic 1, as we will 'manipulate specific aspects of the electrophysiological patterns', by crafting stimulation inputs based on predictive models of individual brain dynamics. Our premise is that such dynamics, when 'manipulated appropriately, might yield the most robust and reliable improvements in behavior', specifically within the domains of attention and cognitive control. We are also highly responsive to Topic 4, as a central feature of our approach is a 'computational model to allow a principled understanding of the algorithms and mechanisms'. Indeed, we will build individualized stimulation inputs using dynamical brain models, deploying an overall validation approach in which 'experimental and computational modeling' are 'mutually informative.' Additionally, the proposed project meets all RFA requirements, in that we: a) use direct systems-level measures of neural activity combined with active causal manipulation (tES+EEG) in awake, behaving human participants; b) address the nature of interactions among specific brain networks (FPN vs. DMN dominance) through a reciprocal and iterative computational/experimental approach (closed-loop modeling and stimulation); c) explicitly test for a well-defined enhancement in cognitive processing (behavioral metrics of cognitive control during task performance); d) use a behavioral task (AX-CPT) that has clear clinical/translational potential; and e) compare our novel model-guided tES approach with conventional spectral EEG methods. Finally, because of the developmental/exploratory and high-risk/high-reward nature of our innovative approach, the project is well-aligned in scope and thrust of the R21 mechanism.

Approach

Overview of Proposed Experiments

Participants. A target of 60 participants will be recruited and enrolled for participation in the study, using standard pre-screening and inclusion/exclusion criteria (see Human Subjects). Participants will primarily be recruited from those participating in the Dual Mechanisms of Cognitive Control (DMCC) project, an on-going research effort led by co-PI Braver, and aimed at characterizing individual differences in the neural mechanisms associated with cognitive control (N~150, aged 18-45, collected at Washington University, St. Louis). This sample population has important advantages, most notably that we have already acquired extensive fMRI and cognitive data on each participant, which has been used to develop and validate fMRI MINDy models. Furthermore, anatomical (head) modeling can be performed by using the existing structural MRI acquired previously from these participants. An additional 10-12 participants will be recruited during an initial pilot testing phase, during which we will fine-tune the tES+EEG protocol and optimize our modeling approach.

Each participant will take part in two 1-hour tES+EEG sessions occurring on separate days (for which they will be compensated $30 per session plus an additional $20 completion bonus, to help minimize attrition). Throughout we will use the terminology of 'delivering tES to a region' to indicate use of a tES montage which optimally targets that region, with the understanding that all calculations/modelling will include the role of volume-conduction. Placement of tES electrodes will be based on single-subject MRI head-modeling to enable focal current delivery over target brain areas ("montage optimization").

Referring to Table 1, Experimental Protocol. The two sessions will differ in tES electrode placement and the task structure. Session 1 is centered on building and validating MINDy models, while Session 2 emphasizes applying this knowledge to identify and manipulate network interactions within attentional/cognitive-control systems.

| | tES Targets | Run 1 | Run 2 | Run 3 |
|---|---|---|---|---|
| Session 1 | V1/2, PCC, dACC, TPJ | Rest | Localizers (Vis/Lang) | Passive-Training [rest] |
| Session 2 | AI, IFG, dlPFC, IPL, SPL | Active-Training [rest] | tES Comparison [rest] | AX-CPT |

Session 1: The first session (see Tab. 1) is open-loop (no EEG-tES feedback) and involves task-free runs both without ('rest') tES and with tES ('passive training') which are used to build MINDy models. These runs are separated by interleaved blocks of two localizer tasks with spatially-random, intermittent DC stimulation. We will use a visual (subjects indicate orientation of Gabor gratings) and language localizer (subjects indicate word/non-word status of visually presented letter strings). The localizer task run is included to provide anatomical constraints and ground-truth data (e.g., occipital visual areas and left inferior frontal language areas) for validating model predictions and source-estimation. The period in between experimental sessions will be used for computing joint MINDy+tES models and pre-calculating initial estimates for optimal control (used in Session 2). Session 2: The second session (on a separate day) includes closed-loop stimulation and is focused on identifying and implementing optimal tES control strategies for attentional modulation. This session has two task free tES+

EEG runs: a first 'active-learning' run, during which closed loop-sampling is used to further calibrate MINDy+tES models and a second run during which conventional (tDCS/tACS) and model-based tES frameworks are directly compared in terms of their ability to manipulate downstream networks (FPN, DMN) via neuromodulation of rAI. In the third run of the session, we will study dynamical features of the brain salience network (with rAI as a core node), and test the ability of this network to modulate reactive cognitive control during performance of the AX-CPT, a well-studied paradigm that has been optimized for sensitivity to the form of control.

tES+EEG Methods. EEG will be collected using a 32-channel dry-electrode wireless EEG platform (g.tec Nautilus). This rapidly deployable cap-based system will sit under a solid mesh housing (OpenBCI) that enables placement of additional recording or stimulating electrodes in a highly customizable configuration. Electrode positions will be digitized using a (to-be-purchased) Polhemus system that enables fast, online registration of electrodes to each participant's MRI. The tES system is implemented with a custom-built design that allows for near real-time modulation of stimulation current and delivery of fully customizable tES waveforms with low latency (see Equipment). Both on-line EEG-guided tES control and EEG processing will be implemented with custom-designed MATLAB/C++ scripts, and through a publicly accessible MINDy code-base.

Optimize MINDy development and validation using tES+EEG. Our prior work has demonstrated the validity, robustness, reliability, and predictive power of MINDy as an individualized, whole-brain neural modeling approach. In so doing, we also validated our underlying algorithms used to optimize MINDy parameter estimation. However, current MINDy models remain imperfect, particularly due to the collinearity of brain data (correlated activity sources). We acknowledge that extending the model-building enterprise to seemingly more complex paradigms, such as tES+EEG, may sound like an additional, high-risk endeavor. However, from an optimization standpoint, adding a known signal (tES) facilitates the model-estimation process, by dissociating mechanisms which would be otherwise correlated. This conjunction of tES with EEG modeling presents a new opportunity to validate the activity prediction mechanisms of the MINDy framework, and further, to correct and calibrate MINDy models by directly training them with tES+EEG data. Further, we test the hypothesis that tES data improves model-estimation and prediction to the extent that tES input signals are maximally informative.

To ensure the robustness of MINDy models, the models will be trained using data from both resting-state EEG (no tES) and from tES+EEG data acquired the passive and active-training runs. The resting-state and 'passive training' runs occurring on Session 1 will be used to build initial off-line estimates of MINDy models following this session, using our Back propagated Kalman Filter algorithm. This technique incorporates the influence of known inputs to a system (i.e., tES) to inform modeling. During the passive learning run, we will collect resting state tES+EEG data while the subject is intermittently administered brief tES impulses to random combinations of four key nodes within the visual, DMN, and salience networks (left V½, left PCC, right dACC, right TPJ). The Session 1 runs are separated by two localizer tasks (see above). The data from the localizer runs will only be used to validate model predictions and the source-localization component of Kalman Filtering.

Figure 28:
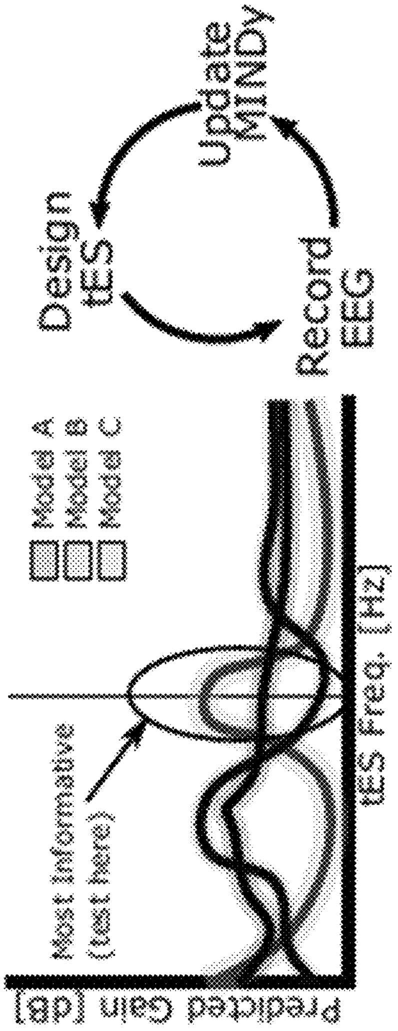
FIG. 28 depicts a schematic of the design of experiments method.

A schematic of the design of experiments method is shown in FIG. 28. Schematic of the Design of Experiments method. Stimulation parameters are chosen for which the resulting EEG will maximally distinguish possible models. This process forms a cycle.

Generating Maximally Informative tES+EEG Data. For each participant, their personalized MINDy model built from Session 1 data will then be deployed in Session 2. In this Session, the 'active-training' data will be used to further refine model parameters in an on-line fashion, using closed-loop identification methods. In particular, will benchmark the performance of 'design of experiments' algorithms including Kriging/DACE methods in improving model estimates, as assessed by prediction of held-out data. These techniques aim to design inputs online that are maximally informative in estimating a model. Conceptually, such methods identify models that each explain the data similarly well, and then use this information to solve for a tES signal that can be used to distinguish the models (i.e., models make very different predictions about its effects).

The active-learning phase will feature DOE-selected tES trials intermixed with validation trials. Validation trials will feature randomly generated inputs (from a wavelet basis set) applied to a set of left-out electrodes. We will hold out data for the is time period following tES for cross-validated comparison. On each trial, a randomly selected DOE algorithm will design a new tES waveform and we will update a single MINDy model (online) based upon the new data. We will compare algorithms, offline, in terms of how well the data generated from their trials improved model predictions (i.e., were trials with tES designed by "X" more informative than trials designed by "Y"?). Our key prediction is that the predictive power of the MINDy simulated EEG time series for the held-out time period will be significantly improved (in terms of R2 fit to the observed data) from the maximally informative DOE trials relative to the original Session 1 MINDy model (estimated prior to the active learning phase).

Compare MINDy-Guided Against Conventional tES for Regulation of Attentional Control Networks.

The influential triple-network account suggests that the SAL network may provide key functionality as an endogenous switching mechanism that enables rapid reconfiguration of attentional control networks (i.e., FPN) in response to salient external or strong task demands, by suppressing the DMN, a brain network that biases attention internally, and which can cause distraction or a loss of focus. Replicating this endogeneous functionality via exogenous inputs remains as a major challenge for current neurostimulation paradigms, yet is widely believed to be critical to achieve cognitive enhancement. We investigate whether such functionality can be achieved by MINDy-guided tES, relying on neural engineering approaches, and comparing them to conventional tES protocols. Currently, there are several unknowns regarding how SAL-driven endogenous switching is implemented in the brain, and as such, how it might be approximated through exogenous neurostimulation. For example, can FPN-DMN switching be triggered through an increase is rAI oscillatory power (AC) or a sustained change in activity (DC)? To test these alternatives, we will compare tACS and tDCS stimulation protocols targeting rAI, using both conventional (naive) approaches, as well as those in which the AC and DC objectives for rAI are optimized directly from MINDy simulations. Additionally, we also test an approach that directly optimizes FPN-DMN balance, via MINDy-guided rAI stimulation, using the reachability metric. In so doing, we provide a systematic exploration of the neural dynamics by which the brain accomplishes modulation of FPN-DMN balance through investigation of different tES approaches. Specifically, we compare stimulation methods in terms of their ability to achieve specific outcome objectives: a) increased FPN broad-band power and coherence; and b) decreases in the analogous quantities for DMN.

In this experiment, occurring during Run 2 of Session 2, participants will undergo resting-state EEG while receiving intermittent (randomly selected) tES stimulation (250 ms every ≈10 s) targeting rAI using 6 different stimulation protocols. In particular, we consider two classes of waveform design: naïve vs. MINDy-optimized; crossed with two stimulation objectives AC vs. DC (2×2). We will use the peak resting-state frequency of rAI within-subject as the AC target frequency. An additional comparison protocol will test the efficacy of MINDy waveforms that are directly optimized to modulate FPN and DMN via rAI. Finally, we also include sham stimulation trials as a baseline control. Thus, there are 6 stimulation types in total: 1) tDCS, 2) tACS, 3) MINDy-optimized for DC (in rAI), 4) MINDy-optimized for AC (in rAI), 5) MINDy-optimized rAI stimulation waveforms that maximize FPN-DMN power, and 6) sham. We evaluate tES effects in terms of broad-band power and coherence in the immediate post-stimulation period (500 msec). Based on prior work demonstrating that network-specific resonant frequencies enable selective communication between brain networks, we hypothesize that DMN and FPN networks will differ in their frequency-response characteristics and thereby can be differentially targeted via AC stimulation. Consequently, our first prediction is that AC neurostimulation protocols (both conventional tACS and MINDy-optimized for AC) will be more effective than DC in altering FPN-DMN power and within-network coherence. Our second key prediction is that MINDy-optimized for AC will be more effective than conventional tACS at achieving the optimal properties via the rAI stimulation site. Finally, we predict that of all 6 stimulation types, the direct-optimization approach will be the most effective in modulating FPN relative to DMN power and coherence.

Alternative Approaches: Model-based solutions to the above problems (FPN vs. DMN power) can be presented as either an open-loop waveform or a closed-loop function of the preceding EEG signal. Closed-loop stimulation is generally more powerful and robust to noise so we will try closed-loop stimulation first, but reserve open-loop as an alternative. If early data suggests that no technique is effective, we will repeat experiments in a new cohort using simultaneous stimulation to both dACC and rAI. If this alternative is successful, we will conclude that rAI requires dACC to initiate modulation, whereas if this approach is also unsuccessful, we will conclude that salience-network modulation of FPN/DMN either requires strong activation (beyond tES safety limits) or is manifest in neuronal events that are not accessible to macroscale stimulation (i.e., due to spatial resolution).

Test effectiveness of MINDy-guided salience network stimulation for cognitive enhancement*We fully leverage the advantages of MINDy, as a formal neural model, to directly optimize neurostimulation objectives (i.e., targeting rAI to modulate FPN vs. DMN power) within a cognitive task context. Specifically, we compare reachability-based tES, with both conventional tACS (and a sham control), and the MINDy-optimized tACS (or tDCS) protocol developed as described above. We utilize the AX-CPT task for this investigation, because it is theoretically interpretable in terms of both how modulation of attention and cognitive control should impact behavioral metrics of task performance, and also because of its high clinical/translational potential. We test the hypothesis that: a) both reachability and MINDy-optimized tES will be superior to conventional tACS (and sham) in improving task performance on high conflict (control demanding) AX-CPT trials; and b) only reachability-based tES will also improve performance on low conflict (less demanding) AX-CPT trials. It is important to note that this embodiment is not contingent on the results of previous embodiments, since a critical question is whether the results obtained from MINDy guided tES in cognitive task contexts can be generalized from those observed under resting-state conditions. For example, a non-intuitive but potential outcome is that the advantages of the MINDy-optimized approach might be more apparent during cognitive task contexts.

Reactive AX-CPT. We will use the AX-CPT as a cognitive task context from which to compare conventional (tACS) and reachability objectives in improving a specific form of cognitive control, termed reactive control. Reactive control, as postulated in our dual-mechanisms of control theoretical framework depends upon rapid detection of competing response tendencies (conflict), as a trigger for retrieval of goal representations and rapid re-orientation of top-down attention. We have postulated that such mechanisms depend upon modulation of the salience network in engaging FPN to over-ride automatic behavioral tendencies potentially mediated by a DMN dominated processing mode. In the AX-CPT, two letter stimuli are presented in sequence (contextual cue and probe) with an intervening delay. Subjects respond with one button for the (A-X) sequence and another button for all other combinations (B-X, B-Y, A-Y). Subjects demonstrate greater cognitive control costs on in trials in which the responses to the individual stimuli conflict (A-Y, B-X) than trials in which the individual stimuli prime congruent responses (A-X, B-Y). We will utilize "reactive" variant of this task, which includes no-go stimuli, a pre-probe cue that indicates indicating whether the trial is high-conflict (BX, AY, no-go) or low-conflict (AX,BY) thereby facilitating goal retrieval and attentional re-orienting when a high-conflict trial is indicated.

During each trial, subjects will receive stimulation to rAI immediately before the pre-probe cue according to one of four tES protocols: sham stimulation (experimental control), tACS, MINDy-optimized tES (using the best MINDy technique for each subject) and reachability-based tES. A first prediction is that MINDy-optimized tES to rAI will engage FPN, thereby promoting retrieval and improving performance (faster RTs, lower error rates) on high conflict trials. Conversely, because MINDy-optimized tES is not state dependent, it will lead to over-control (superfluous cognitive-control expenditure) on low-conflict trials, which should be observable in terms of performance costs (e.g., slowed responses relative to the sham control). In contrast, because reachability-based tES is an enabling rather than forcing technique, it should facilitate network dynamics without pushing activity in a particular direction (i.e., it can result in both increased and decreased FPN activity). As a consequence, our key prediction is that reachability tES is predicted to result in the same benefits as MINDy-optimized tES on high-conflict trials, but should not result in any behavioral costs on low-conflict trials, thus truly optimizing cognitive task performance.

Exemplary embodiments of systems and methods of transcranial electrical stimulation are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A non-invasive closed-loop transcranial electrical stimulation (tES) system, comprising:
- a stimulator configured to generate transcranial electrical current to a head of a subject; and
- a tES computing device, comprising at least one processor in communication with at least one memory device, and the at least one processor programmed to:
  - receive neuroelectrical signals acquired from the head of the subject while being stimulated with the transcranial electrical current; and
  - exogenously modify mechanisms by which electrical activity is generated within a brain of the subject and in response to sensory stimuli presented to the subject via a control loop that uses the neuroelectrical signals to tune a previously estimated electrical Mesoscale Individualized NeuroDynamic (MINDy) model of latent excitatory and inhibitory neural populations for the subject and generates transcranial waveforms based at least in part on the tuned MINDy model.

2. The system of claim 1, wherein the stimulator is configured to generate the transcranial electrical current in response to the received neuroelectrical signals and the generated transcranial waveforms.

3. The system of claim 1, wherein the stimulator is configured to run as an arbitrary waveform generator to generate an arbitrary waveform defined by an input.

4. The system of claim 1, wherein the stimulator comprises:
- a plurality of switches having a cathode and an anode; and
- a microcontroller configured to control the plurality of switches and to provide an anodal stimulation or a cathodal stimulation.

5. The system of claim 4, wherein the microcontroller is controlled in real-time.

6. The system of claim 4, wherein the stimulator further comprises:
- a variable resistance circuitry electrically coupled with the microcontroller,
- wherein the microcontroller is configured to adjust an amplitude of the transcranial electrical current by adjusting resistance in the variable resistance circuitry.

7. The system of claim 4, wherein the stimulator further comprises:
- a current regulator configured to limit a maximum amplitude of the transcranial electrical current.

8. The system of claim 2, wherein the at least one processor is further programmed to:
- individualize the transcranial current to the subject based on magnetoencephalography (MEG) data and/or electroencephalography (EEG) data of the subject.

9. The system of claim 8, wherein the at least one processor is further programmed to:
- individualize the transcranial current to the subject by tuning the electrical MINDy model of the subject based at least in part on the MEG data and/or the EEG data.

10. The system of claim 9, wherein the at least one processor is further programmed to:
- tune the electrical MINDy model based at least in part on resting-state EEG data and EEG data acquired when the subject was under tES.

11. The system of claim 9, wherein the at least one processor is further programmed to tune the electrical MINDy model based on a Kalman filter.

12. The system of claim 9, wherein the electrical MINDy model includes directed connectivity between brain regions of the subject and characteristics of each brain region.

13. The system of claim 9, wherein the at least one processor is further program to:
- optimize the transcranial electrical current based on the electrical MINDy model.

14. The system of claim 1, wherein the at least one processor is further programmed to measure a control objective of the transcranial electrical current based on reachability of the endogenous neural control mechanisms.

15. The system of claim 14, wherein reachability is defined as a reachable set describing patterns of brain activities obtainable by modulating activities of input nodes.

16. The system of claim 14, wherein the at least one processor is further programmed to:
- exogenously modify the brain activities via the control loop by controlling the reachability.

17. The system of claim 16, wherein the at least one processor is further programmed to:
- control the reachability by shifting brain activities to optimize the reachability.

18. The system of claim 16, wherein the at least one processor is further programmed to:
- control the reachability by modifying vector fields of neural states in a brain of the subject.

19. The system of claim 14, wherein the at least one processor is further programmed to determine the reachability based on vector fields of neural states.

20. The system of claim 19, wherein the at least one processor is further programmed to determine the reachability based on the vector fields using a quadratic norm.

* * * * *